(12) United States Patent
Chevrier et al.

(10) Patent No.: US 12,202,892 B2
(45) Date of Patent: Jan. 21, 2025

(54) METHOD OF ADMINISTRATION OF AN ANTI-IFN-α/-ω ANTIBODY

(71) Applicant: Janssen Biotech, Inc., Horsham, PA (US)

(72) Inventors: Marc Chevrier, Collegeville, PA (US); Jarrat Jordan, Norristown, PA (US)

(73) Assignee: Janssen Biotech, Inc., Horsham, PA (US)

( * ) Notice: Subject to any disclaimer, the term of this patent is extended or adjusted under 35 U.S.C. 154(b) by 524 days.

(21) Appl. No.: 16/839,249

(22) Filed: Apr. 3, 2020

(65) Prior Publication Data

US 2020/0317771 A1    Oct. 8, 2020

Related U.S. Application Data

(60) Provisional application No. 62/829,317, filed on Apr. 4, 2019.

(51) Int. Cl.
| | |
|---|---|
| A61K 39/395 | (2006.01) |
| A61K 47/12 | (2006.01) |
| A61K 47/26 | (2006.01) |
| A61P 37/02 | (2006.01) |
| C07K 16/24 | (2006.01) |
| A61K 9/00 | (2006.01) |
| A61K 31/4706 | (2006.01) |
| A61K 31/519 | (2006.01) |
| A61K 31/573 | (2006.01) |
| A61K 39/00 | (2006.01) |

(52) U.S. Cl.
CPC ............ *C07K 16/249* (2013.01); *A61K 47/12* (2013.01); *A61K 47/26* (2013.01); *A61P 37/02* (2018.01); *A61K 9/0019* (2013.01); *A61K 31/4706* (2013.01); *A61K 31/519* (2013.01); *A61K 31/573* (2013.01); *A61K 2039/505* (2013.01); *A61K 2039/54* (2013.01); *A61K 2039/545* (2013.01)

(58) Field of Classification Search
None
See application file for complete search history.

(56) References Cited

U.S. PATENT DOCUMENTS

| | | | |
|---|---|---|---|
| 7,087,726 | B2 | 8/2006 | Chuntharapai et al. |
| 10,208,113 | B2 | 2/2019 | Chi et al. |
| 10,759,854 | B2 * | 9/2020 | Chi .................. A61P 13/12 |
| 2015/0368338 | A1 * | 12/2015 | Chi .................. A61P 7/04 424/136.1 |

FOREIGN PATENT DOCUMENTS

| | | | |
|---|---|---|---|
| EP | 0490233 A1 | 3/1987 | |
| WO | WO02/066649 A2 | 8/2002 | |
| WO | WO05/059106 A2 | 6/2005 | |
| WO | WO06/086586 A2 | 8/2006 | |
| WO | WO09/135861 A2 | 11/2009 | |
| WO | WO-2012162367 A1 * | 11/2012 | ............. A61P 17/00 |
| WO | 2019058345 A2 | 3/2019 | |

OTHER PUBLICATIONS

PCT International Search Report dated Jul. 30, 2020.
Supplementary European Search Report dated Dec. 21, 2022.
Elkon et al., "Type I Interferon and Systemic Lupus Erythematosus," Journal Interferon Cytokine Research, 31(11):803-812 (2011).
Finke et al., "Endogenous type I interferon inducers in autoimmune diseases," Autoimmunity, 42(4):349-352 (2009).
Ghodke, et al., "Systemic lupus erythematosus diagnostics in the 'omics' era," International Journal of Clinical Rheumatology, 8(6): 671-687 (2013).
Janssen Research & Development, et al., "Single Ascending Dose Study in Healthy Participants and Multiple Dose Study of JNJ-55920839 in Participants with Mild to Moderate Systemic Lupus Erythematosus," 2015.
Kalunian et al., "Efficacy and Safety of Rontalizumab (Anti-Interferon Alpha) in SLE Subjects with Restricted Immunosuppressant Use: Results of A Randomized, Double-Blind, Placebo-Controlled Phase 2 Study," 2012 ACR/ARHP Annual Meeting; Abstract #2622 (2012).
McBride et al., "Safety and Pharmacodynamics of Rontalizumab in Patients with Systemic Lupus Erythematosus," Arthritis & Rheumatism, 64(11):3666-3676 (2012).
Merrill et al., "Safety profile and clinical activity of sifalimumab, a fully human anti-interferon α monoclonal antibody, in systemic lupus erythematosus: a phase I, multicentre, double-blind randomized study," Annals of Rheumatological Diseases, 70:1905-1913 (2011).
Petri et al., "Sifalimumab, a Human Anti-Interferon-α Monoclonal Antibody, in Systemic Lupus Erythematosus," Arthritis & Rheumatism, 65(4): 1011-1021 (2013).
Roberts et al., "The Evolution of Type I Interferons," Journal of Interferon and Cytokine Research, 18: 805-816 (1998).
Weissmann, et al., "The Interferon Genes," Progress of Nucleic Acid Research and Molecular Biology, 33: 251-300 (1986).
Yao et al., "Neutralization of Interferon-α/β-Inducible Genes and Downstream Effect in a Phase I Trial of an Anti-Interferon-α Monoclonal Antibody in Systemic Lupus Erythematosus," Arthritis & Rheumatism, 60:1785-1796 (2009).
Yao, et al., "Pharmacokinetics, pharmacodynamics and immunogenicity of JNJ-55920839, an antibody targeting interferon [alpha]/[omega] in healthy subjects and subjects with mild to moderate systemic lupus erythematosus," Clinical Pharmacology in Drug Development, 2019.
UniProt accession No. P05000 (Aug. 12, 2020).

(Continued)

*Primary Examiner* — Yunsoo Kim
(74) *Attorney, Agent, or Firm* — Goodwin Procter LLP

(57) ABSTRACT

Methods for administration of an anti-IFN-α/-ω antibody by subcutaneous or intravenous administration in a clinically proven safe amount are provided. Also provided are methods for clinically proven safe treatment of IFN-I mediated diseases, such as systemic lupus erythematosus (SLE), by subcutaneous or intravenous administration of an anti-IFN-α/-ω antibody.

19 Claims, 6 Drawing Sheets
Specification includes a Sequence Listing.

(56) References Cited

OTHER PUBLICATIONS

"An Investigation of AGS-009 in Patients with Systemic Lupus Erythematosus (SLE)," NCT00960362, Clinical Grials.gov, Last Update Posted Jan. 30, 2012.

"A Study to Evaluate the Long-Term Safety of MEDI-545 in Adult Participants With Systemic Lupus Erythematosus or Myositis," NCT00979654, Last Update Posted Oct. 27, 2016.

"A Study to Evaluate the Efficacy and Safety of Rontalizumab in Patients with Moderately to Severely Active Systemic Lupus Erythematosus," NCT00962832, Last Update Posted Aug. 12, 2016.

JP 2021-558985—Office Action, Mar. 5, 2024, 3 pages.

Kalunian, et al., "A Phase II study of the efficacy and safety of rontalizumab (rhuMAb interferon-α) in patients with systemic lupus erythematosus (ROSE)", Ann Rheum Dis., Jan. 2016, vol. 75, No. 1: pp. 196-202. doi: 10.1136/annrheumdis-2014-206090. Epub Jun. 2, 2015.

* cited by examiner

Part A Healthy Subjects
(n = 48)

Part B SLE Subjects
(n = 32)

★ 6 days safety

*May be dosed on the same day as the final IV cohort
** PK/ADA collection only

SEQUENCE LISTING

<160> NUMBER OF SEQ ID NOS: 35

<210> SEQ ID NO 1
<211> LENGTH: 172
<212> TYPE: PRT
<213> ORGANISM: Homo sapiens

<400> SEQUENCE: 1

Cys Asp Leu Pro Gln Asn His Gly Leu Leu Ser Arg Asn Thr Leu Val
1               5                   10                  15

Leu Leu His Gln Met Arg Arg Ile Ser Pro Phe Leu Cys Leu Lys Asp
            20                  25                  30

Arg Arg Asp Phe Arg Phe Pro Gln Glu Met Val Lys Gly Ser Gln Leu
        35                  40                  45

Gln Lys Ala His Val Met Ser Val Leu His Glu Met Leu Gln Gln Ile
    50                  55                  60

Phe Ser Leu Phe His Thr Glu Arg Ser Ser Ala Ala Trp Asn Met Thr
65                  70                  75                  80

Leu Leu Asp Gln Leu His Thr Gly Leu His Gln Gln Leu Gln His Leu
                85                  90                  95

Glu Thr Cys Leu Leu Gln Val Val Gly Glu Gly Glu Ser Ala Gly Ala
            100                 105                 110

Ile Ser Ser Pro Ala Leu Thr Leu Arg Arg Tyr Phe Gln Gly Ile Arg
        115                 120                 125

Val Tyr Leu Lys Glu Lys Lys Tyr Ser Asp Cys Ala Trp Glu Val Val
    130                 135                 140

Arg Met Glu Ile Met Lys Ser Leu Phe Leu Ser Thr Asn Met Gln Glu
145                 150                 155                 160

Arg Leu Arg Ser Lys Asp Arg Asp Leu Gly Ser Ser
                165                 170

<210> SEQ ID NO 2
<211> LENGTH: 172
<212> TYPE: PRT
<213> ORGANISM: Homo sapiens

<400> SEQUENCE: 2

Cys Asp Leu Pro Gln Asn His Gly Leu Leu Ser Arg Asn Thr Leu Val
1               5                   10                  15

Leu Leu His Gln Met Arg Arg Ile Ser Pro Phe Leu Cys Leu Lys Asp
            20                  25                  30

Arg Arg Asp Phe Arg Phe Pro Gln Glu Met Val Lys Gly Ser Gln Leu
        35                  40                  45

Gln Lys Ala His Val Met Ser Val Leu His Glu Met Leu Gln Gln Ile
    50                  55                  60

Phe Ser Leu Phe His Thr Glu Arg Ser Ser Ala Ala Trp Asn Met Glu
65                  70                  75                  80

Leu Leu Asp Gln Leu His Thr Gly Leu His Gln Gln Leu Gln His Leu
                85                  90                  95

Glu Thr Cys Leu Leu Gln Val Val Gly Glu Gly Glu Ser Ala Gly Ala
            100                 105                 110

Ile Ser Ser Pro Ala Leu Thr Leu Arg Arg Tyr Phe Gln Gly Ile Arg
        115                 120                 125

Val Tyr Leu Lys Glu Lys Lys Tyr Ser Asp Cys Ala Trp Glu Val Val

```
                130               135               140
Arg Met Glu Ile Met Lys Ser Leu Phe Leu Ser Thr Asn Met Gln Glu
145                 150                 155                 160

Arg Leu Arg Ser Lys Asp Arg Asp Leu Gly Ser Ser
                165                 170
```

<210> SEQ ID NO 3
<211> LENGTH: 177
<212> TYPE: PRT
<213> ORGANISM: Pan troglodytes

<400> SEQUENCE: 3

```
Cys Asp Leu Pro Gln Asn His Gly Leu Leu Ser Arg Asn Thr Leu Val
1               5                   10                  15

Leu Leu His Gln Met Arg Arg Ile Ser Pro Phe Leu Cys Leu Lys Asp
                20                  25                  30

Arg Arg Asp Phe Arg Phe Pro Gln Glu Met Val Lys Gly Ser Gln Leu
            35                  40                  45

Gln Lys Ala Gln Val Met Ser Val Leu His Glu Met Leu Gln Gln Ile
        50                  55                  60

Phe Ser Leu Phe His Thr Glu Arg Ser Ser Ala Ala Trp Asn Met Thr
65                  70                  75                  80

Leu Leu Asp Gln Leu His Thr Gly Leu His Gln Gln Leu Gln His Leu
                85                  90                  95

Glu Thr Cys Leu Leu Gln Val Met Gly Glu Gly Glu Ser Ala Gly Ala
                100                 105                 110

Ile Ser Ser Pro Ala Leu Thr Leu Arg Arg Tyr Phe Gln Gly Ile Arg
            115                 120                 125

Val Tyr Leu Lys Glu Lys Lys Tyr Ser Asp Cys Ala Trp Glu Val Val
        130                 135                 140

Arg Met Glu Ile Met Lys Ser Leu Phe Leu Ser Thr Asn Met Gln Glu
145                 150                 155                 160

Arg Leu Arg Ser Lys Asp Arg Asp Leu Gly Ser Ser Arg Asn Asp Ser
                165                 170                 175

His
```

<210> SEQ ID NO 4
<211> LENGTH: 172
<212> TYPE: PRT
<213> ORGANISM: Macaca fascicularis

<400> SEQUENCE: 4

```
Cys Asp Leu Pro Gln Asn His Gly Leu Leu Ser Arg Asn Thr Leu Val
1               5                   10                  15

Leu Leu His Gln Met Arg Arg Ile Ser Pro Phe Leu Cys Leu Lys Asp
                20                  25                  30

Arg Arg Asp Phe Arg Phe Pro Gln Glu Met Val Glu Gly Ser Gln Leu
            35                  40                  45

Gln Lys Ala Gln Val Met Ser Val Leu His Glu Met Leu Gln Gln Ile
        50                  55                  60

Phe Ser Leu Phe His Thr Glu His Ser Ser Ala Ala Trp Asn Thr Thr
65                  70                  75                  80

Leu Leu Asp His Leu His Thr Gly Leu His Arg Gln Leu Glu His Leu
                85                  90                  95

Glu Thr Cys Leu Val Gln Val Met Arg Glu Gly Glu Ser Ala Gly Ala
                100                 105                 110
```

Ile Arg Ser Pro Ala Leu Thr Leu Arg Arg Tyr Phe Gln Gly Ile Arg
            115                 120                 125

Val Tyr Leu Lys Glu Lys Tyr Ser Asp Cys Ala Trp Val Val Val
    130                 135                 140

Arg Met Glu Ile Met Lys Ser Leu Phe Leu Ser Thr Asn Met Gln Glu
145                 150                 155                 160

Arg Leu Lys Ser Lys Asp Gly Asp Leu Gly Ser Ser
            165                 170

<210> SEQ ID NO 5
<211> LENGTH: 165
<212> TYPE: PRT
<213> ORGANISM: Homo sapiens

<400> SEQUENCE: 5

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 6
<211> LENGTH: 166
<212> TYPE: PRT
<213> ORGANISM: Homo sapiens

<400> SEQUENCE: 6

Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
            20                  25                  30

Arg His Asp Phe Glu Phe Pro Gln Glu Glu Phe Asp Asp Lys Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Leu Asp Glu Thr
65                  70                  75                  80

Leu Leu Asp Glu Phe Tyr Ile Glu Leu Asp Gln Gln Leu Asn Asp Leu
                85                  90                  95

Glu Ser Cys Val Met Gln Val Gly Val Ile Ser Pro Leu Met
                100                 105                 110

Tyr Glu Asp Ser Ile Leu Ala Val Arg Lys Tyr Phe Gln Arg Ile Thr
            115                 120                 125

Leu Tyr Leu Thr Glu Lys Lys Tyr Ser Ser Cys Ala Trp Glu Val Val
130                 135                 140

Arg Ala Glu Ile Met Arg Ser Phe Ser Leu Ser Ile Asn Leu Gln Lys
145                 150                 155                 160

Arg Leu Lys Ser Lys Glu
                165

<210> SEQ ID NO 7
<211> LENGTH: 166
<212> TYPE: PRT
<213> ORGANISM: Homo sapiens

<400> SEQUENCE: 7

Cys Asp Leu Pro Gln Thr His Ser Leu Gly Asn Arg Arg Ala Leu Ile
1               5                   10                  15

Leu Leu Gly Gln Met Gly Arg Ile Ser Pro Phe Ser Cys Leu Lys Asp
            20                  25                  30

Arg His Asp Phe Arg Ile Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Ile Glu Arg Lys Tyr Ser Pro Cys Ala Trp Glu Val Val
130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 8
<211> LENGTH: 166
<212> TYPE: PRT
<213> ORGANISM: Homo sapiens

<400> SEQUENCE: 8

Cys Asp Leu Pro Glu Thr His Ser Leu Asp Asn Arg Arg Thr Leu Met
1               5                   10                  15

Leu Leu Ala Gln Met Ser Arg Ile Ser Pro Ser Ser Cys Leu Met Asp
            20                  25                  30

Arg His Asp Phe Gly Phe Pro Gln Glu Glu Phe Asp Gly Asn Gln Phe
        35                  40                  45

Gln Lys Ala Pro Ala Ile Ser Val Leu His Glu Leu Ile Gln Gln Ile
    50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
            85                  90                  95

Glu Ala Cys Val Met Gln Glu Arg Val Gly Glu Thr Pro Leu Met
            100                 105                 110

Asn Val Asp Ser Ile Leu Ala Val Lys Lys Tyr Phe Arg Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Leu Ser Leu Ser Thr Asn Leu Gln Glu
145                 150                 155                 160

Arg Leu Arg Arg Lys Glu
                165

<210> SEQ ID NO 9
<211> LENGTH: 166
<212> TYPE: PRT
<213> ORGANISM: Homo sapiens

<400> SEQUENCE: 9

Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Thr Trp Glu Gln Ser
65                  70                  75                  80

Leu Leu Glu Lys Phe Ser Thr Glu Leu Asn Gln Gln Leu Asn Asp Met
            85                  90                  95

Glu Ala Cys Val Ile Gln Glu Val Gly Val Glu Thr Pro Leu Met
            100                 105                 110

Asn Val Asp Ser Ile Leu Ala Val Lys Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Leu Ser Lys Ile Phe Gln Glu
145                 150                 155                 160

Arg Leu Arg Arg Lys Glu
                165

<210> SEQ ID NO 10
<211> LENGTH: 166
<212> TYPE: PRT
<213> ORGANISM: Homo sapiens

<400> SEQUENCE: 10

Cys Asp Leu Pro Gln Thr His Ser Leu Ser Asn Arg Arg Thr Leu Met
1               5                   10                  15

Ile Met Ala Gln Met Gly Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

```
Phe Asn Leu Phe Ser Thr Lys Asp Ser Ser Ala Thr Trp Asp Glu Thr
 65                  70                  75                  80

Leu Leu Asp Lys Phe Tyr Thr Glu Leu Tyr Gln Gln Leu Asn Asp Leu
                 85                  90                  95

Glu Ala Cys Met Met Gln Glu Val Gly Val Glu Asp Thr Pro Leu Met
            100                 105                 110

Asn Val Asp Ser Ile Leu Thr Val Arg Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Leu Ser Ala Asn Leu Gln Glu
145                 150                 155                 160

Arg Leu Arg Arg Lys Glu
                165

<210> SEQ ID NO 11
<211> LENGTH: 166
<212> TYPE: PRT
<213> ORGANISM: Homo sapiens

<400> SEQUENCE: 11

Cys Asn Leu Ser Gln Thr His Ser Leu Asn Asn Arg Arg Thr Leu Met
  1               5                  10                  15

Leu Met Ala Gln Met Arg Arg Ile Ser Pro Phe Ser Cys Leu Lys Asp
                 20                  25                  30

Arg His Asp Phe Glu Phe Pro Gln Glu Glu Phe Asp Gly Asn Gln Phe
             35                  40                  45

Gln Lys Ala Gln Ala Ile Ser Val Leu His Glu Met Met Gln Gln Thr
         50                  55                  60

Phe Asn Leu Phe Ser Thr Lys Asn Ser Ser Ala Ala Trp Asp Glu Thr
 65                  70                  75                  80

Leu Leu Glu Lys Phe Tyr Ile Glu Leu Phe Gln Gln Met Asn Asp Leu
                 85                  90                  95

Glu Ala Cys Val Ile Gln Glu Val Gly Val Glu Glu Thr Pro Leu Met
            100                 105                 110

Asn Glu Asp Ser Ile Leu Ala Val Lys Lys Tyr Phe Gln Arg Ile Thr
            115                 120                 125

Leu Tyr Leu Met Glu Lys Lys Tyr Ser Pro Cys Ala Trp Glu Val Val
        130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 12
<211> LENGTH: 166
<212> TYPE: PRT
<213> ORGANISM: Homo sapiens

<400> SEQUENCE: 12

Cys Asp Leu Pro Gln Thr His Ser Leu Gly Asn Arg Arg Ala Leu Ile
  1               5                  10                  15

Leu Leu Ala Gln Met Gly Arg Ile Ser Pro Phe Ser Cys Leu Lys Asp
                 20                  25                  30

Arg Pro Asp Phe Gly Leu Pro Gln Glu Glu Phe Asp Gly Asn Gln Phe
             35                  40                  45
```

```
Gln Lys Thr Gln Ala Ile Ser Val Leu His Glu Met Ile Gln Gln Thr
 50                  55                  60

Phe Asn Leu Phe Ser Thr Glu Asp Ser Ser Ala Ala Trp Glu Gln Ser
 65                  70                  75                  80

Leu Leu Glu Lys Phe Ser Thr Glu Leu Tyr Gln Gln Leu Asn Asn Leu
                 85                  90                  95

Glu Ala Cys Val Ile Gln Glu Val Gly Met Glu Glu Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
130                 135                 140

Arg Ala Glu Ile Met Arg Ser Leu Ser Phe Ser Thr Asn Leu Gln Lys
145                 150                 155                 160

Ile Leu Arg Arg Lys Asp
                165

<210> SEQ ID NO 13
<211> LENGTH: 166
<212> TYPE: PRT
<213> ORGANISM: Homo sapiens

<400> SEQUENCE: 13

Cys Asp Leu Pro Gln Thr His Ser Leu Arg Asn Arg Arg Ala Leu Ile
  1               5                  10                  15

Leu Leu Ala Gln Met Gly Arg Ile Ser Pro Phe Ser Cys Leu Lys Asp
                 20                  25                  30

Arg His Glu Phe Arg Phe Pro Glu Glu Glu Phe Asp Gly His Gln Phe
             35                  40                  45

Gln Lys Thr Gln Ala Ile Ser Val Leu His Glu Met Ile Gln Gln Thr
 50                  55                  60

Phe Asn Leu Phe Ser Thr Glu Asp Ser Ser Ala Ala Trp Glu Gln Ser
 65                  70                  75                  80

Leu Leu Glu Lys Phe Ser Thr Glu Leu Tyr Gln Gln Leu Asn Asp Leu
                 85                  90                  95

Glu Ala Cys Val Ile Gln Glu Val Gly Val Glu Glu Thr Pro Leu Met
            100                 105                 110

Asn Glu Asp Phe Ile Leu Ala Val Arg Lys Tyr Phe Gln Arg Ile Thr
        115                 120                 125

Leu Tyr Leu Met Glu Lys Lys Tyr Ser Pro Cys Ala Trp Glu Val Val
130                 135                 140

Arg Ala Glu Ile Met Arg Ser Phe Ser Phe Ser Thr Asn Leu Lys Lys
145                 150                 155                 160

Gly Leu Arg Arg Lys Asp
                165

<210> SEQ ID NO 14
<211> LENGTH: 166
<212> TYPE: PRT
<213> ORGANISM: Homo sapiens

<400> SEQUENCE: 14

Cys Asp Leu Pro Gln Thr His Ser Leu Gly His Arg Arg Thr Met Met
  1               5                  10                  15

Leu Leu Ala Gln Met Arg Arg Ile Ser Leu Phe Ser Cys Leu Lys Asp
                 20                  25                  30
```

```
Arg His Asp Phe Arg Phe Pro Gln Glu Glu Phe Asp Gly Asn Gln Phe
            35                  40                  45

Gln Lys Ala Glu Ala Ile Ser Val Leu His Glu Val Ile Gln Gln Thr
 50                  55                  60

Phe Asn Leu Phe Ser Thr Lys Asp Ser Ser Val Ala Trp Asp Glu Arg
 65                  70                  75                  80

Leu Leu Asp Lys Leu Tyr Thr Glu Leu Tyr Gln Gln Leu Asn Asp Leu
                 85                  90                  95

Glu Ala Cys Val Met Gln Glu Val Trp Val Gly Gly Thr Pro Leu Met
                100                 105                 110

Asn Glu Asp Ser Ile Leu Ala Val Arg Lys Tyr Phe Gln Arg Ile Thr
                115                 120                 125

Leu Tyr Leu Thr Glu Lys Lys Tyr Ser Pro Cys Ala Trp Glu Val Val
            130                 135                 140

Arg Ala Glu Ile Met Arg Ser Phe Ser Ser Arg Asn Leu Gln Glu
145                 150                 155                 160

Arg Leu Arg Arg Lys Glu
                165

<210> SEQ ID NO 15
<211> LENGTH: 166
<212> TYPE: PRT
<213> ORGANISM: Homo sapiens

<400> SEQUENCE: 15

Cys Asp Leu Pro Gln Thr His Ser Leu Gly Asn Arg Arg Ala Leu Ile
 1               5                  10                  15

Leu Leu Ala Gln Met Gly Arg Ile Ser His Phe Ser Cys Leu Lys Asp
                 20                  25                  30

Arg His Asp Phe Gly Phe Pro Glu Glu Glu Phe Asp Gly His Gln Phe
            35                  40                  45

Gln Lys Thr Gln Ala Ile Ser Val Leu His Glu Met Ile Gln Gln Thr
 50                  55                  60

Phe Asn Leu Phe Ser Thr Glu Asp Ser Ser Ala Ala Trp Glu Gln Ser
 65                  70                  75                  80

Leu Leu Glu Lys Phe Ser Thr Glu Leu Tyr Gln Gln Leu Asn Asp Leu
                 85                  90                  95

Glu Ala Cys Val Ile Gln Glu Val Gly Val Glu Glu Thr Pro Leu Met
                100                 105                 110

Asn Val Asp Ser Ile Leu Ala Val Arg Lys Tyr Phe Gln Arg Ile Thr
                115                 120                 125

Leu Tyr Leu Thr Glu Lys Lys Tyr Ser Pro Cys Ala Trp Glu Val Val
            130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 16
<211> LENGTH: 166
<212> TYPE: PRT
<213> ORGANISM: Homo sapiens

<400> SEQUENCE: 16

Cys Asp Leu Pro Gln Thr His Ser Leu Gly Asn Arg Arg Ala Leu Ile
 1               5                  10                  15
```

-continued

Leu Leu Ala Gln Met Gly Arg Ile Ser His Phe Ser Cys Leu Lys Asp
           20                  25                  30

Arg Tyr Asp Phe Gly Phe Pro Gln Glu Val Phe Asp Gly Asn Gln Phe
       35                  40                  45

Gln Lys Ala Gln Ala Ile Ser Ala Phe His Glu Met Ile Gln Gln Thr
   50                  55                  60

Phe Asn Leu Phe Ser Thr Lys Asp Ser Ser Ala Ala Trp Asp Glu Thr
65                  70                  75                  80

Leu Leu Asp Lys Phe Tyr Ile Glu Leu Phe Gln Gln Leu Asn Asp Leu
               85                  90                  95

Glu Ala Cys Val Thr Gln Glu Val Gly Val Glu Ile Ala Leu Met
           100                 105                 110

Asn Glu Asp Ser Ile Leu Ala Val Arg Lys Tyr Phe Gln Arg Ile Thr
               115                 120                 125

Leu Tyr Leu Met Gly Lys Lys Tyr Ser Pro Cys Ala Trp Glu Val Val
   130                 135                 140

Arg Ala Glu Ile Met Arg Ser Phe Ser Phe Ser Thr Asn Leu Gln Lys
145                 150                 155                 160

Gly Leu Arg Arg Lys Asp
               165

<210> SEQ ID NO 17
<211> LENGTH: 165
<212> TYPE: PRT
<213> ORGANISM: Homo sapiens

<400> SEQUENCE: 17

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
           20                  25                  30

Arg His Asp Phe Gly Phe Pro Gln Glu Glu Phe Gly Asn Gln Phe Gln
       35                  40                  45

Lys Ala Glu Thr Ile Pro Val Leu His Glu Met Ile Gln Gln Ile Phe
   50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
               85                  90                  95

Ala Cys Val Ile Gln Gly Val Gly Val Thr Glu Thr Pro Leu Met Lys
           100                 105                 110

Glu Asp Ser Ile Leu Ala Val Arg Lys Tyr Phe Gln Arg Ile Thr Leu
               115                 120                 125

Tyr Leu Lys Glu Lys Lys Tyr Ser Pro Cys Ala Trp Glu Val Val Arg
   130                 135                 140

Ala Glu Ile Met Arg Ser Phe Ser Leu Ser Thr Asn Leu Gln Glu Ser
145                 150                 155                 160

Leu Arg Ser Lys Glu
               165

<210> SEQ ID NO 18
<211> LENGTH: 166
<212> TYPE: PRT
<213> ORGANISM: Homo sapiens

<400> SEQUENCE: 18

```
Cys Asp Leu Pro Glu Thr His Ser Leu Asp Asn Arg Arg Thr Leu Met
1               5                   10                  15

Leu Leu Ala Gln Met Ser Arg Ile Ser Pro Ser Ser Cys Leu Met Asp
            20                  25                  30

Arg His Asp Phe Gly Phe Pro Gln Glu Glu Phe Asp Gly Asn Gln Phe
            35                  40                  45

Gln Lys Ala Pro Ala Ile Ser Val Leu His Glu Leu Ile Gln Gln Ile
50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
            85                  90                  95

Glu Ala Cys Val Met Gln Glu Glu Arg Val Gly Glu Thr Pro Leu Met
            100                 105                 110

Asn Ala Asp Ser Ile Leu Ala Val Lys Lys Tyr Phe Arg Arg Ile Thr
            115                 120                 125

Leu Tyr Leu Thr Glu Lys Lys Tyr Ser Pro Cys Ala Trp Glu Val Val
130                 135                 140

Arg Ala Glu Ile Met Arg Ser Leu Ser Leu Ser Thr Asn Leu Gln Glu
145                 150                 155                 160

Arg Leu Arg Arg Lys Glu
                165

<210> SEQ ID NO 19
<211> LENGTH: 166
<212> TYPE: PRT
<213> ORGANISM: Homo sapiens

<400> SEQUENCE: 19

Cys Asp Leu Pro Gln Thr His Ser Leu Gly Asn Arg Arg Ala Leu Ile
1               5                   10                  15

Leu Leu Ala Gln Met Gly Arg Ile Ser His Phe Ser Cys Leu Lys Asp
            20                  25                  30

Arg His Asp Phe Gly Phe Pro Glu Glu Glu Phe Asp Gly His Gln Phe
            35                  40                  45

Gln Lys Ala Gln Ala Ile Ser Val Leu His Glu Met Ile Gln Gln Thr
50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
            85                  90                  95

Glu Ala Cys Val Ile Gln Glu Val Gly Val Glu Glu Thr Pro Leu Met
            100                 105                 110

Asn Glu Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 20
<211> LENGTH: 166
<212> TYPE: PRT
```

<213> ORGANISM: Homo sapiens

<400> SEQUENCE: 20

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 21
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Met Ala Leu Thr Phe Tyr Leu Leu Val Ala Leu Val Val Leu Ser Tyr
1               5                   10                  15

Lys Ser Phe Ser Ser Leu Gly
            20

<210> SEQ ID NO 22
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Met Ala Arg Ser Phe Ser Leu Leu Met Val Val Leu Val Leu Ser Tyr
1               5                   10                  15

Lys Ser Ile Cys Ser Leu Gly
            20

<210> SEQ ID NO 23
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Met Ala Leu Pro Phe Ala Leu Leu Met Ala Leu Val Val Leu Ser Cys
1               5                   10                  15

Lys Ser Ser Cys Ser Leu Asp
            20

<210> SEQ ID NO 24
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Met Ala Leu Ser Phe Ser Leu Leu Met Ala Val Leu Val Leu Ser Tyr
1               5                   10                  15

Lys Ser Ile Cys Ser Leu Gly
            20

<210> SEQ ID NO 25
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Met Ala Leu Thr Phe Ala Leu Leu Val Ala Leu Leu Val Leu Ser Cys
1               5                   10                  15

Lys Ser Ser Cys Ser Val Gly
            20

<210> SEQ ID NO 26
<211> LENGTH: 557
<212> TYPE: PRT
<213> ORGANISM: Homo sapiens

<400> SEQUENCE: 26

Met Met Val Val Leu Leu Gly Ala Thr Thr Leu Val Leu Val Ala Val
1               5                   10                  15

Ala Pro Trp Val Leu Ser Ala Ala Gly Gly Lys Asn Leu Lys Ser
                20                  25                  30

Pro Gln Lys Val Glu Val Asp Ile Ile Asp Asp Asn Phe Ile Leu Arg
            35                  40                  45

Trp Asn Arg Ser Asp Glu Ser Val Gly Asn Val Thr Phe Ser Phe Asp
        50                  55                  60

Tyr Gln Lys Thr Gly Met Asp Asn Trp Ile Lys Leu Ser Gly Cys Gln
65                  70                  75                  80

Asn Ile Thr Ser Thr Lys Cys Asn Phe Ser Ser Leu Lys Leu Asn Val
                85                  90                  95

Tyr Glu Glu Ile Lys Leu Arg Ile Arg Ala Glu Lys Glu Asn Thr Ser
            100                 105                 110

Ser Trp Tyr Glu Val Asp Ser Phe Thr Pro Phe Arg Lys Ala Gln Ile
        115                 120                 125

Gly Pro Pro Glu Val His Leu Glu Ala Glu Asp Lys Ala Ile Val Ile
    130                 135                 140

His Ile Ser Pro Gly Thr Lys Asp Ser Val Met Trp Ala Leu Asp Gly

```
            145                 150                 155                 160
        Leu Ser Phe Thr Tyr Ser Leu Val Ile Trp Lys Asn Ser Ser Gly Val
                        165                 170                 175
        Glu Glu Arg Ile Glu Asn Ile Tyr Ser Arg His Lys Ile Tyr Lys Leu
                        180                 185                 190
        Ser Pro Glu Thr Thr Tyr Cys Leu Lys Val Lys Ala Ala Leu Leu Thr
                        195                 200                 205
        Ser Trp Lys Ile Gly Val Tyr Ser Pro Val His Cys Ile Lys Thr Thr
                        210                 215                 220
        Val Glu Asn Glu Leu Pro Pro Glu Asn Ile Glu Val Ser Val Gln
        225                 230                 235                 240
        Asn Gln Asn Tyr Val Leu Lys Trp Asp Tyr Thr Tyr Ala Asn Met Thr
                        245                 250                 255
        Phe Gln Val Gln Trp Leu His Ala Phe Leu Lys Arg Asn Pro Gly Asn
                        260                 265                 270
        His Leu Tyr Lys Trp Lys Gln Ile Pro Asp Cys Glu Asn Val Lys Thr
                        275                 280                 285
        Thr Gln Cys Val Phe Pro Gln Asn Val Phe Gln Lys Gly Ile Tyr Leu
                        290                 295                 300
        Leu Arg Val Gln Ala Ser Asp Gly Asn Asn Thr Ser Phe Trp Ser Glu
        305                 310                 315                 320
        Glu Ile Lys Phe Asp Thr Glu Ile Gln Ala Phe Leu Leu Pro Pro Val
                        325                 330                 335
        Phe Asn Ile Arg Ser Leu Ser Asp Ser Phe His Ile Tyr Ile Gly Ala
                        340                 345                 350
        Pro Lys Gln Ser Gly Asn Thr Pro Val Ile Gln Asp Tyr Pro Leu Ile
                        355                 360                 365
        Tyr Glu Ile Ile Phe Trp Glu Asn Thr Ser Asn Ala Glu Arg Lys Ile
                        370                 375                 380
        Ile Glu Lys Lys Thr Asp Val Thr Val Pro Asn Leu Lys Pro Leu Thr
        385                 390                 395                 400
        Val Tyr Cys Val Lys Ala Arg Ala His Thr Met Asp Glu Lys Leu Asn
                        405                 410                 415
        Lys Ser Ser Val Phe Ser Asp Ala Val Cys Glu Lys Thr Lys Pro Gly
                        420                 425                 430
        Asn Thr Ser Lys Ile Trp Leu Ile Val Gly Ile Cys Ile Ala Leu Phe
                        435                 440                 445
        Ala Leu Pro Phe Val Ile Tyr Ala Ala Lys Val Phe Leu Arg Cys Ile
        450                 455                 460
        Asn Tyr Val Phe Phe Pro Ser Leu Lys Pro Ser Ser Ile Asp Glu
        465                 470                 475                 480
        Tyr Phe Ser Glu Gln Pro Leu Lys Asn Leu Leu Leu Ser Thr Ser Glu
                        485                 490                 495
        Glu Gln Ile Glu Lys Cys Phe Ile Ile Glu Asn Ile Ser Thr Ile Ala
                        500                 505                 510
        Thr Val Glu Glu Thr Asn Gln Thr Asp Glu Asp His Lys Lys Tyr Ser
                        515                 520                 525
        Ser Gln Thr Ser Gln Asp Ser Gly Asn Tyr Ser Asn Glu Asp Glu Ser
                        530                 535                 540
        Glu Ser Lys Thr Ser Glu Glu Leu Gln Gln Asp Phe Val
        545                 550                 555

<210> SEQ ID NO 27
```

```
<211> LENGTH: 331
<212> TYPE: PRT
<213> ORGANISM: Homo sapiens

<400> SEQUENCE: 27

Met Leu Leu Ser Gln Asn Ala Phe Ile Phe Arg Ser Leu Asn Leu Val
1               5                   10                  15

Leu Met Val Tyr Ile Ser Leu Val Phe Gly Ile Ser Tyr Asp Ser Pro
            20                  25                  30

Asp Tyr Thr Asp Glu Ser Cys Thr Phe Lys Ile Ser Leu Arg Asn Phe
        35                  40                  45

Arg Ser Ile Leu Ser Trp Glu Leu Lys Asn His Ser Ile Val Pro Thr
    50                  55                  60

His Tyr Thr Leu Leu Tyr Thr Ile Met Ser Lys Pro Glu Asp Leu Lys
65                  70                  75                  80

Val Val Lys Asn Cys Ala Asn Thr Thr Arg Ser Phe Cys Asp Leu Thr
                85                  90                  95

Asp Glu Trp Arg Ser Thr His Glu Ala Tyr Val Thr Val Leu Glu Gly
            100                 105                 110

Phe Ser Gly Asn Thr Thr Leu Phe Ser Cys Ser His Asn Phe Trp Leu
        115                 120                 125

Ala Ile Asp Met Ser Phe Glu Pro Pro Glu Phe Glu Ile Val Gly Phe
    130                 135                 140

Thr Asn His Ile Asn Val Met Val Lys Phe Pro Ser Ile Val Glu Glu
145                 150                 155                 160

Glu Leu Gln Phe Asp Leu Ser Leu Val Ile Glu Glu Gln Ser Glu Gly
                165                 170                 175

Ile Val Lys Lys His Lys Pro Glu Ile Lys Gly Asn Met Ser Gly Asn
            180                 185                 190

Phe Thr Tyr Ile Ile Asp Lys Leu Ile Pro Asn Thr Asn Tyr Cys Val
        195                 200                 205

Ser Val Tyr Leu Glu His Ser Asp Glu Gln Ala Val Ile Lys Ser Pro
    210                 215                 220

Leu Lys Cys Thr Leu Leu Pro Pro Gly Gln Glu Ser Glu Ser Ala Glu
225                 230                 235                 240

Ser Ala Lys Ile Gly Gly Ile Ile Thr Val Phe Leu Ile Ala Leu Val
                245                 250                 255

Leu Thr Ser Thr Ile Val Thr Leu Lys Trp Ile Gly Tyr Ile Cys Leu
            260                 265                 270

Arg Asn Ser Leu Pro Lys Val Leu Arg Gln Gly Leu Ala Lys Gly Trp
        275                 280                 285

Asn Ala Val Ala Ile His Arg Cys Ser His Asn Ala Leu Gln Ser Glu
    290                 295                 300

Thr Pro Glu Leu Lys Gln Ser Ser Cys Leu Ser Phe Pro Ser Ser Trp
305                 310                 315                 320

Asp Tyr Lys Arg Ala Ser Leu Cys Pro Ser Asp
                325                 330

<210> SEQ ID NO 28
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28
```

```
Glu Val Gln Leu Val Gln Ser Gly Ala Glu Val Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
            35                  40                  45

Gly Ile Ile Asp Pro Ser Asp Ser Asp Thr Arg Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Pro Gly Leu Asn Trp Ala Pro Asp Phe Asp Tyr Trp Gly
                100                 105                 110

Gln Gly Thr Leu Val Thr Val Ser Ser
            115                 120

<210> SEQ ID NO 29
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Asn Ser
            20                  25                  30

Tyr Leu Asn Trp Tyr Gln Gln Lys Pro Gly Lys Ala Pro Lys Leu Leu
            35                  40                  45

Ile Tyr Gly Ala Ser Ser Leu Gln Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Gly Tyr Asp Phe Pro
                85                  90                  95

Leu Thr Phe Gly Gln Gly Thr Lys Val Glu Ile Lys
                100                 105

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Ser Ile Asp Asn Ser Tyr
1               5

<210> SEQ ID NO 31
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 31

Gly Ala Ser
1

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Gln Gly Tyr Asp Phe Pro Leu Thr
1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Tyr Ser Phe Thr Ser Tyr Trp
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ile Asp Pro Ser Asp Ser Asp Thr
1               5

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Arg His Pro Gly Leu Asn Trp Ala Pro Asp Phe Asp Tyr
1               5                   10
```

METHOD OF ADMINISTRATION OF AN ANTI-IFN-α/-ω ANTIBODY

CROSS-REFERENCE TO RELATED APPLICATIONS

This application claims the benefit of U.S. Provisional Patent Application Ser. No. 62/829,317, filed 4 Apr. 2019, the entire contents of which are incorporated herein by reference in their entireties.

REFERENCE TO SEQUENCE LISTING SUBMITTED ELECTRONICALLY

This application contains a Sequence Listing, which is submitted electronically via EFS-Web as an ASCII formatted sequence listing with a file name "JBI6068USNP1Seglist.txt" creation date of Apr. 4, 2019 and having a size of about 43 kb. The sequence listing submitted via EFS-Web is part of the specification and is herein incorporated by reference in its entirety.

FIELD OF THE INVENTION

The invention relates to methods of administration of an anti-IFN-α/-ω antibody in a clinically proven safe amount and methods of treating an IFN-I mediated disease by subcutaneous or intravenous administration of an anti-IFN-α/-ω antibody in a clinically proven safe amount.

BACKGROUND OF THE INVENTION

Type I interferons (IFNs) (IFN-I) are a family of cytokines that signal through a ubiquitously expressed heterodimeric receptor IFNAR (heterodimer of IFNAR1 and IFNAR2) resulting in antiviral, antiproliferative and immunomodulatory effects. In humans, type I IFN is composed of at least 12 IFN-α protein subtypes and 1 subtype each for IFN-β, IFN-ε, IFN-κ, and IFN-ω. IFN-I release occurs in response to both microbial and sterile ligands.

The IFN-I family of cytokines signal through the ubiquitously expressed heterodimeric IFN-α receptor (IFNAR). Type I IFN can be induced by both microbial and endogenous factors (Elkon & Stone, Journal Interferon Cytokine Res., 31(11):803-812 (2011); Finke et al., Autoimmunity, 42(4):349-352 (2009)). IFN is rapidly produced in response to infectious agents, such as viruses, to help control infection. Microbial agents, endogenous ligands (e.g., necrotic cells), and immune complexes can trigger IFN-I production by activating both toll-like receptor (TLR)-dependent and TLR-independent pathways. The resulting IFN-I binds to the IFNAR resulting in the activation of antiviral, antiproliferative, and immunomodulatory genes. This so-called IFN-inducible gene signature has been observed in many autoimmune diseases.

Several immune-mediated inflammatory diseases or autoimmune diseases, such as lupus, including Systemic Lupus Erythematosus (SLE) and cutaneous lupus erythematosus (CLE), type I diabetes, psoriasis, Sjögren's disease, systemic sclerosis, rheumatoid arthritis, immune thrombocytopenia (ITP), Aicardi-Goutieres syndrome (AGS), myositis, common variable immune deficiency (CVID) and autoimmune thyroid disease are associated, at least in a subpopulation of patients, with overexpression of IFN-inducible gene transcripts commonly called the IFN signature present in whole blood and/or tissue, or with elevated IFN-I.

SLE is a chronic autoimmune or immune-mediated inflammatory disease in which pathogenic T cell, B cell and innate immune responses result in inflammation and tissue damage across multiple organ systems. The disease displays a broad range of symptoms with heterogeneous clinical presentation and can include systemic, cutaneous, renal, musculoskeletal, neurological and hematological manifestations. SLE varies greatly in severity and is chronic, remitting or relapsing with flares of activity cycling with periods of improvement or remission that can last weeks, months, or years.

IFN-α is elevated in SLE patients and is believed to promote a loss of tolerance to self-antigens. IFN-α has been shown to contribute to sustained dendritic cell activation and thus antigen presentation, and suppression of Treg function contributing to SLE. IFN-α also induces BLyS expression, a target for the marketed SLE therapeutic BENLYSTA™. A number of polymorphisms associated with production or response to IFN-I have been identified and account for over half of confirmed polymorphisms associated with SLE (Ghodke-Puranik & Niewold, International journal of clinical rheumatology 8, doi:10.2217/ijr.13.58 (2013)). Antibodies neutralizing various IFN-α subtypes (pan-IFN-α antibodies) are being evaluated in clinical trials for SLE (see, for example, Int. Pat. Publ. No. WO02/066649, Int Pat. Publ. No. WO05/059106, Int. Pat. Publ. No. WO06/086586, Int. Pat. Publ. No. WO09/135861).

In addition to IFN-αs, IFN-ω can represent a key additional subclass of type 1 IFN that is overexpressed in SLE patients. SLE patients are known to produce autoantibodies to IFNs, and in two studies, the highest levels of nascent autoantibodies were against IFN-ω, implying that IFN-ω can be more prevalent in some SLE patients than other classes of IFN (McBride et al., Arthritis Rheum., 64(11): 3666-3676 (2012); Petri et al., Arthritis Rheum., 65(4):1011-1021 (2013)). The anti-IFN-α antibodies currently in clinical trials (sifalimumab (MEDI-545), rontalizumab and AGS-009) do not neutralize IFN-ω. Clinical trial data with these antibodies indicate partial reduction of the type I IFN signature in patients after treatment with anti-IFN-α antibodies (Merrill et al., Ann Rheum Dis 70:1905-1913, 2011; Yao et al., Arthritis Rheum 60:1785-1796, 2009), and Phase 2 trial data with rontalizumab (a pan-anti-IFN-α antibody) indicated improvement in signs and symptoms of SLE, flare rates, and steroid burden at week 24 in a pre-specified biomarker defined group of Interferon Signature Metric (ISM)-Low moderate to severely active lupus subjects. No efficacy was seen in patients having higher levels of IFN-inducible gene expression pre-defined as ISM-High (Kalunian et al., 2012 ACR/ARHP Annual Meeting; Abstract #2622, 2012).

Current standard of care for SLE includes corticosteroids, antimalarial drugs, immunosuppressants or B cell modulators. These therapeutics can exhibit toxicity and other serious side effects and can not be suitable for treatment of all lupus patients. Thus, there is a need for additional therapeutic treatments for SLE and other IFN-I mediated diseases.

BRIEF SUMMARY OF THE INVENTION

The invention relates to the clinically proven safe administration of an anti-IFN-α/-ω antibody to subjects, including for clinically proven safe treatment of an IFN-I mediated disease in a subject, such as systemic lupus erythematosus (SLE).

In one general aspect, the invention relates to a method of providing clinically proven safe administration of an anti- IFN-α/-ω antibody to a human subject in need thereof, comprising subcutaneously or intravenously administering to the subject a pharmaceutical composition comprising the antibody and a pharmaceutically acceptable carrier, wherein the antibody comprises a heavy chain variable region and a light chain variable region, the heavy chain variable region comprising heavy chain complementarity determining regions (HCDRs) HCDR1, HCDR2 and HCDR3 amino acid sequences of SEQ ID NOs: 33, 34, and 35, respectively, and the light chain variable region comprising light chain complementarity determining regions (LCDRs) LCDR1, LCDR2 and LCDR3 amino acid sequences of SEQ ID NOs: 30, 31, and 32, respectively, and wherein a total dosage of the antibody administered is 0.1 mg/kg to 20 mg/kg body weight of the subject per administration.

In one embodiment, the anti-IFN-α/-ω antibody comprises a heavy chain variable region (VH) having the amino acid sequence of SEQ ID NO: 28 and a light chain variable region (VL) having the amino acid sequences of SEQ ID NO: 29.

In one embodiment, the pharmaceutical composition is administered intravenously. In such embodiments, the total dosage of the anti-IFN-α/-ω antibody administered per administration is 0.1 mg/kg, 0.3 mg/kg, 1 mg/kg, 3 mg/kg, 10 mg/kg, 15 mg/kg or 20 mg/kg body weight of the subject, or any dosage in between.

In one embodiment, the pharmaceutical composition is administered subcutaneously. In such embodiments, the total dosage of the anti-IFN-α/-ω antibody administered per administration is 0.1 mg/kg, 0.3 mg/kg, 0.5 mg/kg, 0.7 mg/kg, 1 mg/kg, 1.2 mg/kg, 1.5 mg/kg, 1.7 mg/kg, 2 mg/kg, 2.3 mg/kg or 2.5 mg/kg body weight of the subject, or any dosage in between.

In one embodiment, the administration of the pharmaceutical composition achieves, in the plasma of the subject, at least one parameter selected from: (i) an area under the concentration time curve $(AUC)_{(0-t)}$ of about 50 μg·day/mL to about 7000 μg·day/mL, and (ii) a maximum concentration observed ($C_{max}$) of about 5 μg/mL to about 500 μg/mL.

In one embodiment, the administration of the anti-IFN-α/-ω antibody does not result in production of antibodies against the anti-IFN-α/-ω antibody in the subject.

In another general aspect, the invention relates to a method of providing clinically proven safe treatment of an IFN-I mediated disease in a human subject in need thereof, the method comprising subcutaneously or intravenously administering to the subject a pharmaceutical composition comprising the antibody and a pharmaceutically acceptable carrier, wherein the antibody comprises a heavy chain variable region and a light chain variable region, the heavy chain variable region comprising heavy chain complementarity determining regions (HCDRs) HCDR1, HCDR2 and HCDR3 amino acid sequences of SEQ ID NOs: 33, 34, and 35, respectively, and the light chain variable region comprising light chain complementarity determining regions (LCDRs) LCDR1, LCDR2 and LCDR3 amino acid sequences of SEQ ID NOs: 30, 31, and 32, respectively, and wherein a total dosage of the antibody administered is 0.1 mg/kg to 20 mg/kg body weight of the subject per administration.

In one embodiment, the IFN-I mediated disease is selected from systemic lupus erythematosus (SLE), type I diabetes, psoriasis, primary Sjögren's disease, systemic sclerosis, rheumatoid arthritis, transplant rejection, dermatomyositis, polymyositis, Aicardi-Goutières syndrome, Sting associated vasculopathy with onset in infancy (SAVI) or chronic atypical neutrophilic dermatosis with lipodystrophy and elevated temperature syndrome (CANDLE). Preferably, the disease is systemic lupus erythematosus (SLE), and more preferably, mild to moderate SLE.

In one embodiment, the anti-IFN-α/-ω antibody comprises a heavy chain variable region (VH) having the amino acid sequence of SEQ ID NO: 28 and a light chain variable region (VL) having the amino acid sequences of SEQ ID NO: 29.

In one embodiment, the anti-IFN-α/-ω antibody is an IgG1 isotype. Some variation exists within the IgG1 constant domain (e.g. well-known allotypes), with variation at positions 214, 356, 358, 422, 431, 435 or 436 (residue numbering according to the EU numbering) (see e.g., IMGT Web resources; IMGT Repertoire (IG and TR); Proteins and alleles; allotypes). The anti-IFN-α/-ω antibody may be of any IgG1 allotype, such as G1m17, G1m3, G1 m1, G1m2, G1m27 or G1m28.

In one embodiment, the pharmaceutical composition is administered to the human subject intravenously for no less than 30 minutes in a total dosage of the anti-IFN-α/-ω antibody administered of 10 mg/kg body weight of the subject per administration, preferably the pharmaceutical composition is intravenously administered to the human subject repeatedly, more preferably once every two weeks.

In one embodiment, the administration of the pharmaceutical composition achieves, in the plasma of the subject, at least one parameter selected from: (i) an area under the concentration time curve $(AUC)_{(0-14d)}$ of about 1000 μg·day/mL to about 3500 μg·day/mL, and (ii) a maximum concentration observed ($C_{max}$) of about 120 μg/mL to about 400 μg/mL.

In one embodiment, the human subject, by day 100 after the administration of the pharmaceutical composition, has at least one of clinical responses selected from i) a reduction in the Systemic Lupus Erythematosus Responder Index (SRI); ii) no new British Isles Lupus Assessment Group (BILAG) A or 2B shifts; iii) a reduction in the Systemic Lupus Erythematosus Disease Activity Index 2000 (SLEDAI-2K) from baseline; iv) a reduction in the Systemic Lupus Erythematosus 2000 Responder Index-50 (S2K RI-50) from baseline; and v) a reduction in the Physician's Global Assessment of Disease Activity (PGA) from baseline.

In one embodiment, the human subject achieves a steady-state condition of the antibody within 40-50 days after administration.

In one embodiment, the administration of the anti-IFN-α/-ω antibody does not result in a treatment emergent adverse event (TEAE) related to a malignancy or anaphylactic or serum sickness-type reaction in the subject.

In another general aspect, the method of the invention further comprises:
a. assaying gene expression of one or more genes DHX58, EIF2AK2, HERC5, IFI44, IFI44L, IFI6, IRF7, PARP9, PLSCR1 and SAMD9L in a biological sample of the human subject; and
b. identifying the human subject as responsive to treatment of the antibody prior to administering to the subject the pharmaceutical composition comprising the antibody and the pharmaceutically acceptable carrier.

The details of one or more embodiments of the invention are set forth in the description below. Other features and advantages will be apparent from the following detailed description, and the appended claims.

BRIEF DESCRIPTION OF THE DRAWINGS

The foregoing summary, as well as the following detailed description of the invention, will be better understood when read in conjunction with the appended drawings. It should be understood that the invention is not limited to the precise embodiments shown in the drawings.

DETAILED DESCRIPTION OF THE INVENTION

Figure 1:
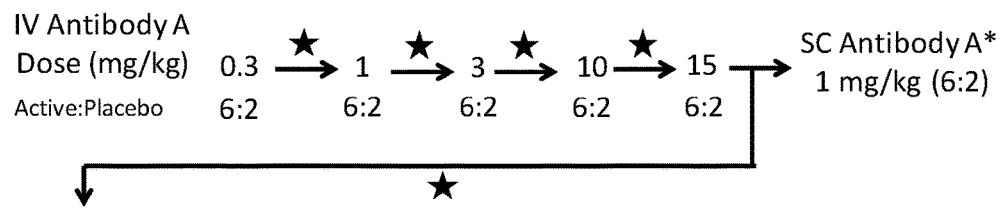
FIG. 1 shows a diagrammatic representation of the study design of a clinical study using an anti-IFN-α/-ω antibody (ANTIBODY A) according to an embodiment of the application.
Figure 1:
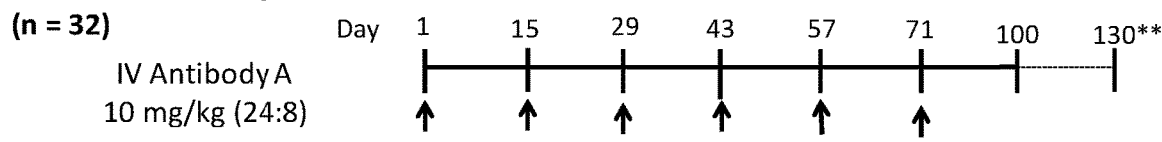

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein.

It must be noted that as used herein and in the appended claims, the singular forms "a," "an," and "the" include plural reference unless the context clearly dictates otherwise.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising", "containing", "including", and "having", whenever used herein in the context of an aspect or embodiment of the invention can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "subject" refers to a mammalian subject, preferably human, diagnosed with or suspected of having an IFN-I mediated disease, whom will be or has been administered an anti-IFN-α/-ω antibody according to a method of the invention. Diagnosis of an IFN-I mediated disease can be done by a clinician according to clinical diagnostic testing, physical examination of the subject, or any other accepted method for diagnosing a subject with a particular disease.

A used herein, "a subject suspected of having an IFN-I mediated disease" is a subject that presents signs or symptoms indicative of an IFN-I mediated disease that are discernable to a clinician and/or the subject, but whose suspected diagnosis has not been confirmed by clinical diagnostic testing, physical examination of the subject, or other accepted method for diagnosing a subject with the suspected IFN-I mediated disease.

Examples of IFN-I mediated diseases include, but are not limited to, Systemic Lupus Erythematosus (SLE), cutaneous lupus erythematosus (CLE), type I diabetes, psoriasis, Sjögren's disease, systemic sclerosis, rheumatoid arthritis, immune thrombocytopenia (ITP), Aicardi-Goutieres syndrome (AGS), myositis, common variable immune deficiency (CVID), autoimmune thyroid disease, transplant rejection, dermatomyositis, polymyositis, Sting associated vasculopathy with onset in infancy (SAVI), and chronic atypical neutrophilic dermatosis with lipodystrophy and elevated temperature syndrome (CANDLE).

The term "type I interferon" or "IFN-I" refers to all native subtypes of human interferon-α and one subtype of interferon-β, interferon-ε, interferon-ω and interferon-κ which bind to a common interferon receptor IFNAR.

The term "interferon-α" (IFN-α) as used herein refers to all native subtypes of human alpha interferons. Native IFN-α consists of at least 12 closely related protein subtypes encoded by distinct genes with a high degree of structural homology (Weissmann and Weber, Prog Nucl Acid Res Mol Biol., 33: 251, 1986; Roberts et al., J Interferon Cytokine Res. 18: 805-816, 1998). Nomenclature for human interferons is found at: http://www_genenames_org/gene-families/_IFN. Table 1 below shows the sequences of the IFN-α subtypes used herein, in addition to other Type I IFNs.

The term IFN-ω as used herein refers to human IFN-ω having the amino acid sequence shown in SEQ ID NO: 1 and UniProt accession number P05000. Human IFN-ω also includes the variant of SEQ ID NO: 2 having a threonine to glutamic acid substitution at position 80 (T80).

The IFN-α subtypes and IFN-ω can also be produced by recombinant expression using standard methods. Exemplary signal sequences that can be used for directing secretion are shown in SEQ ID NOs: 21-25.

As used herein the term "IFNAR" refers to the well-known interferon receptor which is a heterodimer of IFNAR1 and IFNAR2. IFNAR1 and IFNAR2 protein sequences are shown in SEQ ID NOs: 26 and 27, respectively. IFNAR1 mature extracellular domain spans residues 28-436 of SEQ ID NO: 26 and IFNAR2 mature extracellular domain spans residues 27-243 of SEQ ID NO: 27.

TABLE 1

| IFN Protein | Alternative Name | GenBank Accession Number Adopted | SEQ ID NO: |
|---|---|---|---|
| IFN-αA | IFN-α2s | V00549 | 5 |
| IFN-αB2 | IFN-α6 | X03125 | 6 |
| IFN-αC | IFN-α10 | NM_002171.1 | 7 |
| IFN-αD | Val114 IFN-α1 | V00538 | 8 |
| IFN-αF | IFN-α21 | V00540 | 9 |
| IFN-αG | IFN-α5 | X02956 | 10 |
| IFN-αH2 | IFN-α14 | X02959 | 11 |
| IFN-αI | IFN-α17 | V00532 | 12 |
| IFN-αJ1 | IFN-α7 | X02960 | 13 |
| IFN-αK | IFN-α6 | X02958 | 14 |
| IFN-α4b | IFN-α4 | X02955 | 15 |
| IFN-αWA | IFN-α16 | X02957 | 16 |
| IFN-α2 | IFN-α2b | V00548, NM_00605.2 | 17 |
| IFN-α1 | Ala114 IFN-αD | J00210 | 18 |
| IFN-α4a | IFN-αM1 | NM_021068 | 19 |
| IFN-β | | V00534 | 20 |
| IFN-ω | | NM_002177.1 | 1 |
| IFN-ω T80E | | | 2 |
| Chimp IFN-ω | | XM_528554.1 | 3 |
| Cyno IFN-ω | | NA | 4 |

As used herein, an "an anti-IFN-α/-ω antibody," refers to an engineered fully human monoclonal antibody (mAb) of the IgG1κsubtype, or antigen binding fragment thereof, that binds and neutralizes at least 10 human interferon alpha (IFN-α) subtypes at an affinity of $1 \times 10^{-10}$ M or less and further binds and neutralizes human interferon omega (IFN-ω) with high affinity. Preferably, the anti-IFN-α/-ω antibody does not bind or neutralize interferon beta (IFN-0). Examples of anti-IFN-α/-ω antibody or antigen binding fragment thereof useful for the invention include, but are not limited to, IFWM3405, IFWM3442, IFWM3525, IFWM3423, IFWM3444, IFWM3421, or other anti-IFN-α/-ω antibodies or fragments thereof described in U.S. Pat. No. 10,208,113, the content of which is herein incorporated by reference in its entirety. In a preferred embodiment, the anti-IFN-α/-ω antibody neutralizes at least 11 out of the 12 IFN alphas. In another preferred embodiment, the anti-IFN-α/-ω antibody comprises a heavy chain variable region and a light chain variable region, the heavy chain variable region comprising heavy chain complementarity determining regions (HCDRs) HCDR1, HCDR2 and HCDR3 amino acid sequences of SEQ ID NOs: 33, 34, and 35, respectively, and the light chain variable region comprising light chain complementarity determining regions (LCDRs) LCDR1, LCDR2 and LCDR3 amino acid sequences of SEQ ID NOs: 30, 31, and 32, respectively. In one embodiment, the anti-IFN-α/-ω antibody comprises a heavy chain variable region (VH) having the amino acid sequence of SEQ ID NO: 28 and a light chain variable region (VL) having the amino acid sequences of SEQ ID NO: 29. In a preferred embodiment, the anti-IFN-α/-ω antibody is a humanized or fully human immunoglobulin.

Anti-IFN-α/-ω antibodies can be prepared by any method known in the art in view of the present disclosure for preparing monoclonal antibodies including, but not limited to, hybridoma production. For example, anti-IFN-α/-ω antibodies can be produced in a mammalian cell line (e.g., Chinese Hamster Ovary (CHO) cell line) using recombinant DNA technology. In particular, methods of producing anti-IFN-α/-ω antibodies useful for the invention are further described in, e.g., U.S. Pat. No. 10,208,113, which is herein incorporated by reference.

The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments that bind to a mammalian IFN-α/-ω. For example, antibody fragments capable of binding to INF-α/-ω or portions thereof, including, but not limited to, Fab (e.g., by papain digestion), Fab' (e.g., by pepsin digestion and partial reduction) and F(ab')2 (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')2 heavy chain portion can be designed to include DNA sequences encoding the CH1 domain and/or hinge region of the heavy chain. The various portions of antibodies can be joined together chemically by conventional techniques or can be prepared as a contiguous protein using genetic engineering techniques.

As used herein, the term "human antibody" refers to an antibody in which substantially every part of the protein (e.g., CDR, framework, CL, CH domains (e.g., CH1, CH2, CH3), hinge, (VL, VH)) is substantially non-immunogenic in humans, with only minor sequence changes or variations. A "human antibody" can also be an antibody that is derived from or closely matches human germline immunoglobulin sequences. Human antibodies can include amino acid residues not encoded by germline immunoglobulin sequences (e.g., mutations introduced by random or site-specific mutagenesis in vitro or by somatic mutation in vivo). Often, this means that the human antibody is substantially non-immunogenic in humans. Human antibodies have been classified into groupings based on their amino acid sequence similarities. Accordingly, using a sequence similarity search, an antibody with a similar linear sequence can be chosen as a template to create a human antibody. Similarly, antibodies designated primate (monkey, baboon, chimpanzee, etc.), rodent (mouse, rat, rabbit, guinea pig, hamster, and the like) and other mammals designate such species, sub-genus, genus, sub-family, and family specific antibodies. Further, chimeric antibodies can include any combination of the above. Such changes or variations optionally and preferably retain or reduce the immunogenicity in humans or other species relative to non-modified antibodies. Thus, a human antibody is distinct from a chimeric or humanized antibody.

It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

The term "safe," as it relates to a dose, dosage regimen, treatment or method with an anti-IFN-α/-ω antibody refers to a favorable risk:benefit ratio with an acceptable frequency and/or acceptable severity of treatment-emergent adverse events (referred to as AEs or TEAEs) compared to the standard of care or to another comparator in accordance with the Federal Food, Drug, and Cosmetic Act, as amended (secs. 201-902, 52 Stat. 1040 et seq., as amended; 21 U.S.C. §§ 321-392). In particular, safe as it relates to a dose, dosage regimen, or treatment with an anti-IFN-α/-ω antibody of the present invention refers to with an acceptable frequency and/or acceptable severity of adverse events associated with administration of the antibody if attribution is considered to be possible, probable, or very likely due to the use of the anti-IFN-α/-ω antibody. Safety is often measured by toxicity testing to determine the highest tolerable dose or the optimal dose of an active pharmaceutical ingredient needed to achieve the desired benefit. Studies that look at safety also seek to identify any potential adverse effects that can result from exposure to the drug.

As used herein, unless otherwise noted, the term "clinically proven" (used independently or to modify the term "safe") shall mean that it has been proven by a clinical study in human subjects wherein the clinical study has met the approval standards of U.S. Food and Drug Administration, European Medicines Evaluation Agency (EMEA), or a corresponding national regulatory agency. In one embodiment of the application, the clinical study is a phase 1, randomized, double-blind, placebo-controlled, single ascending dose study of an anti-IFN-α/-ω antibody in healthy human subjects. Preferably, the clinical study further comprises a multiple dose study of an anti-IFN-α/-ω antibody in human subjects with mild to moderate systemic lupus erythematosus.

As used herein, the phrases "adverse event," "treatment-emergent adverse event," and "adverse reaction" mean any harm, unfavorable, unintended or undesired sign or outcome associated with or caused by administration of a pharmaceutical composition or therapeutic. However, abnormal values or observations are not reported as adverse events unless considered clinically significant by the investigator. As used herein, when referring to an adverse event, "clinically apparent" means clinically significant as determined by a medical doctor or an investigator using standard acceptable to those of ordinary skill in the art. When the harm or undesired outcome of adverse events reaches such a level of severity, a regulatory agency can deem the pharmaceutical composition or therapeutic unacceptable for the proposed use. Examples of adverse events or reactions when used in the context of subcutaneous or intravenous administration of an anti-IFN-α/-ω antibody include, but are not limited to, infections and infestations, such as rhinitis, herpes zoster, and myringitis bullosa; respiratory, thoracic and mediastinal disorders, such as cough, throat irritation, and oropharyngeal pain; gastrointestinal disorders, such as diarrhea and flatulence; nervous system disorders, such as headache and dizziness; blood and lymphatic system disorders, such as anaemia and lymphadenopathy; back pain, premature labour, infusion reactions, local injection site reactivity, malignancy and no anaphylactic or serum sickness-type reactions.

As used herein, "treatment" or "treat" refers to therapeutic treatment. Individuals in need of treatment include those subjects diagnosed with the disorder or a symptom of the disorder. Subjects that can be treated also include those prone to or susceptible to have the disorder, of those in which the disorder is to be prevented. Beneficial or desired clinical results include alleviation of symptoms, diminishment of extent of disease, stabilized (i.e., not worsening) state of disease, delay or slowing of disease progression, amelioration or palliation of the disease state, and remission (whether partial or total), whether detectable or undetectable. Beneficial clinical result includes, in a subject who has received treatment, for example reduced proliferation of B cells or dendritic cells, reduction of inflammatory cytokines, adhesion molecules, proteases, immunoglobulins, combinations thereof, increased production of anti-inflammatory proteins, a reduction in the number of autoreactive cells, an increase in immune tolerance, inhibition of autoreactive cell survival, and/or a decrease in one or more symptoms mediated by IFN-I. Clinical response can be assessed using screening techniques such as magnetic resonance imaging (MRI) scan, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, chromatography, and the like.

The terms "efficacy" and "effective" as used herein in the context of a dose, dosage regimen, treatment or method refer to the effectiveness of a particular dose, dosage or treatment regimen. Efficacy can be measured based on change in the course of the disease in response to an agent of the present invention. For example, an anti-IFN-α/-ω antibody useful for the present invention is administered to a subject in an amount and for a time sufficient to induce an improvement, preferably a sustained improvement, in at least one indicator that reflects the severity of the disorder that is being treated. Various indicators that reflect the extent of the subject's illness, disease or condition can be assessed for determining whether the amount and time of the treatment is sufficient. Such indicators include, for example, clinically recognized indicators of disease severity, symptoms, or manifestations of the disorder in question. The degree of improvement generally is determined by a physician, who can make this determination based on signs, symptoms, biopsies, or other test results, and who can also employ questionnaires that are administered to the subject, such as quality-of-life questionnaires developed for a given disease. For example, an anti-IFN-α/-ω antibody of the present invention can be administered to achieve an improvement in a subject's condition related to SLE.

Improvement on SLE can be evaluated by at least one of the following clinical response assessments: i) a reduction in the Systemic Lupus Erythematosus Responder Index (SRI), such as by 1 point, 2 points, 3 points, 4 points, 5 points, or 6 points; ii) a shift in British Isles Lupus Assessment Group (BILAG); iii) a reduction in the Systemic Lupus Erythematosus Disease Activity Index 2000 (SLEDAI-2K) from baseline; iv) a reduction in the Systemic Lupus Erythematosus 2000 Responder Index-50 (S2K RI-50) from baseline; v) a reduction in the Physician's Global Assessment of Disease Activity (PGA) from baseline; vi) the change and percent change from baseline in Cutaneous Lupus Erythematosus Disease Area and Severity Index (CLASI) activity and damage scores; vii) the change and percent change from baseline in norm-based scores of SF-36, SF-36 physical and mental component summary scores; and viii) the change and percent change from baseline in EuroQol-5 dimensions-5 levels (EQ-5D-5L) scale.

In addition, joint assessment is used to evaluate the clinical response, e.g., the change from baseline in the number of joints with pain and signs of inflammation over time for subjects. Each of the joints are evaluated for tenderness and swelling (hips excluded for swelling) at all specified visits by an assessor.

In some embodiments, before subject to a treatment according to an embodiment of the application, a human subject having mild to moderate SLE is defined by:
1) Systemic Lupus International Collaborating Clinics (SLICC) criteria for diagnosis of lupus with at least 1 Systemic Lupus Erythematosus Disease Activity Index 2000 (SLEDAI-2K)-defined non-serologic clinical activity within 3 months prior to treatment, and
2) Serologically positive within 2 months prior to:
   a) a positive anti-nuclear antibody (ANA) titer of ≥1:80, or
   b) a positive anti-double stranded deoxyribonucleic acid test (note: if Anti-dsDNA is done by enzyme-linked immunosorbent assay, a test 2× upper limit of normal is required to be considered unequivocally positive) or
   c) a positive anti-Smith antibody and/or positive anti-ribonucleoprotein (RNP) antibody and/or anti-Ro antibody, and in addition to at least one of the above:
   d) a positive lupus IFN profile score during screening.

The responsiveness of a subject to a treatment can be measured by an index of disease activity, clinical symptoms or by any other measure of disease activity. As used herein, a "patient not responsive or poorly responsive to a treatment" refers to a patient who has no or minimal improvement after the treatment.

As used herein, a dosage amount of an anti-IFN-α/-ω antibody in "mg/kg" refers to the amount of the anti-IFN-α/-ω antibody in milligrams per kilogram of the body weight of a subject to be administered with the antibody.

In one general aspect, the invention relates to a method of providing clinically proven safe subcutaneous and/or intravenous administration of an anti-IFN-α/-ω antibody to a human subject in need thereof. Preferably, the subject is diagnosed with or suspected of having an IFN-I mediated disease, in which the IFN-I levels are elevated. There is an association between elevated levels of type I interferons (IFN-I) and several human autoimmune diseases such as systemic sclerosis, Sjögren's syndrome, type I diabetes and autoimmune thyroid disease, and most notably, systemic lupus erythematosus (SLE). Examples of an IFN-mediated disease with which a subject to be administered an anti-IFN-α/-ω antibody or antigen binding fragment thereof according methods of the invention can be diagnosed with or suspected of having include, but are not limited to, an autoimmune disease, such as systemic lupus erythematosus (SLE), type I diabetes, psoriasis, primary Sjögren's disease, systemic sclerosis, rheumatoid arthritis, transplant rejection, dermatomyositis, polymyositis, Aicardi-Goutieres syndrome, Sting associated vasculopathy with onset in infancy (SAVI) or chronic atypical neutrophilic dermatosis with lipodystrophy and elevated temperature syndrome (CANDLE).

In one preferred embodiment, the subject is diagnosed with or suspected of having SLE. SLE can target many organs and tissues, including the skin, blood vessels, muscles, kidneys and lungs. Preclinical and clinical data support a role for IFN-α and IFN-ω in the initiation and progression of SLE.

In one embodiment, a method of providing clinically proven safe administration of an anti-IFN-α/-ω antibody to a subject and/or safe treatment of an IFN-mediated disease, preferably SLE in a human subject, comprises subcutaneously or intravenously administering to the subject a pharmaceutical composition comprising an anti-IFN-α/-ω antibody and a pharmaceutically acceptable carrier, wherein a total dosage of the anti-IFN-α/-ω antibody administered is 0.1 mg/kg to 20 mg/kg body weight of the subject per administration.

In one embodiment, the pharmaceutical composition is administered subcutaneously. Subcutaneous administration refers to administration under the skin, in which a drug or therapeutic is injected into the tissue layer between the skin and muscle. Medication administered via subcutaneous administration is usually absorbed more slowly than if injected into a vein. When administration of an anti-IFN-α/-ω antibody is via subcutaneous injection, the total dosage of the an anti-IFN-α/-ω antibody to be administered to the subject per administration can be administered in a single subcutaneous injection, or in multiple subcutaneous injections, such as 1, 2, 3, 4, 5, or more subcutaneous injections.

In another embodiment, the pharmaceutical composition is administered intravenously. Intravenous administration refers to administration directly into a vein. Intravenous administration can be via injection (e.g., with a syringe at higher pressures) or via infusion (e.g., using the pressure supplied by gravity). Intravenous administration is typically the quickest method for delivering a drug or therapeutic throughout the body, because the drug or therapeutic is carried by circulation. When administration of an anti-IFN-α/-ω antibody is via intravenous administration, administration can be by intravenous infusion or injection, and is preferably via infusion. For example, the total dosage of an anti-IFN-α/-ω antibody to be administered to the subject per administration can be administered by intravenous infusion over a period of time, such as about 30 minutes to 180 minutes, preferably 60 minutes to 120 minutes, such as 30 minutes, 60 minutes, 90 minutes, 120 minutes, 150 minutes, or 180 minutes, or any duration in between.

The total dosage of an anti-IFN-α/-ω antibody per administration is selected so as to provide safe administration and/or safe treatment by subcutaneous or intravenous administration as determined in clinical trials. According to embodiments of the invention, when the pharmaceutical composition is administered intravenously, a total dosage of the anti-IFN-α/-ω antibody administered per administration is, for example, 0.1 mg/kg, 0.3 mg/kg, 0.5 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, or any dosage in between. When the pharmaceutical composition is administered subcutaneously, a total dosage of the anti-IFN-α/-ω antibody administered per administration is, for example, 0.1 mg/kg, 0.3 mg/kg, 0.5 mg/kg, 0.7 mg/kg, 1 mg/kg, 1.2 mg/kg, 1.5 mg/kg, 1.7 mg/kg, 2 mg/kg, 2.3 mg/kg, 2.5 mg/kg, or any dosage in between.

The total dosage of the anti-IFN-α/-ω antibody can be administered once per day, once per week, once per two weeks, once per month, once every six months, etc. for a period of one day, one week, one month, six months, 1 year, 2 years or longer. For example, a total dosage of 0.1 mg/kg to 2.5 mg/kg of the anti-IFN-α/-ω antibody can be administered per administration (e.g., once per day for at least one day) by a single subcutaneous injection, or multiple subcutaneous injections (e.g., 2 to 5 injections) at substantially the same time, i.e., over a time of period of 0 minutes to 1 hour, such as 5 minutes, 10 minutes, 15 minutes, 20 minutes, 25 minutes, 30 minutes, 35 minutes, 40 minutes, 45 minutes, 50 minutes, 55 minutes, or 1 hour. Alternatively, a total dosage of 0.3 mg/kg to 20 mg/kg of the anti-IFN-α/-ω antibody can be administered per administration (e.g., once per day for at least one day) by intravenous infusion over a time period of about 30 minutes to 3 hours, preferably 60 minutes to 120 minutes. Multiple administrations of the anti-IFN-α/-ω antibody, each at a total dosage of 0.3 mg/kg to 20 mg/kg, can be administered to a subject in need thereof.

Pharmaceutical compositions suitable for use in the methods of the invention are formulated for subcutaneous administration or intravenous administration. Examples of formulations suitable for subcutaneous and/or intravenous administration include, but are not limited to, solutions, suspensions, emulsions, and dry products that can be dissolved or suspended in a pharmaceutically acceptable carrier for injection or infusion. In a preferred embodiment, a pharmaceutical composition comprising an anti-IFN-α/-ω antibody for use in the methods of the invention is formulated as a solution.

A concentration of an anti-IFN-α/-ω antibody included in pharmaceutical compositions used in the invention can vary. Typically, the concentration of the anti-IFN-α/-ω antibody is 1 mg/mL to 100 mg/mL, such as 1 mg/mL, 10 mg/mL, 20 mg/mL, 30 mg/mL, 40 mg/mL, 50 mg/mL, 60 mg/mL, 70 mg/mL, 80 mg/mL, 90 mg/mL, or 100 mg/mL, or any concentration in between. Preferably, the concentration of the anti-IFN-α/-ω antibody is 40 mg/mL to 60 mg/mL, for instance 50 mg/mL.

Pharmaceutical compositions for use in the invention further comprise one or more pharmaceutically acceptable carriers, such as those widely employed in the art of drug manufacturing, and particularly antibody drug manufacturing. As used herein, the term "carrier" refers to any excipient, diluent, buffer, stabilizer, or other material well known in the art for pharmaceutical formulations. Pharmaceutically acceptable carriers in particular are non-toxic and should not interfere with the efficacy of the active ingredient. The pharmaceutically acceptable carriers include excipients and/or additives suitable for use in the pharmaceutical compositions known in the art, e.g., as listed in "Remington: The Science & Practice of Pharmacy", 19th ed., Williams & Williams, (1995), and in the "Physician's Desk Reference", 52nd ed., Medical Economics, Montvale, N.J. (1998), the disclosures of which are entirely incorporated herein by reference.

According to embodiments of the invention, a pharmaceutical composition for use in the invention comprises an anti-IFN-α/-ω antibody and a pharmaceutically acceptable carrier. In some embodiments, the pharmaceutically acceptable carrier comprises one or more carbohydrates, such as lactose, maltose, sucrose, one or more surfactants, such as polysorbate 20, polysorbate 80, and one or more acids and/or salts, such as lactic acid, sodium lactate, acetic acid, sodium acetate. Preferably, the pharmaceutical composition has a pH of 5 to 6, such as a pH of 5.0, 5.1, 5.2, 5.3, 5.4, 5.5, 5.6, 5.7, 5.8, 5.9, or 6.0, or any value in between.

In some embodiments, a pharmaceutical composition for use in the invention comprises sucrose, lactose, and/or maltose at a concentration of 1% to 10% weight by volume (w/v), such as 5% to 10% (w/v). For example, the concentration of sucrose, lactose, and/or maltose can be 1% (w/v), 1.5% (w/v), 2% (w/v), 2.5% (w/v), 3% (w/v), 3.5% (w/v), 4% (w/v), 4.5% (w/v), 5% (w/v), 5.5% (w/v), 6% (w/v), 6.5% (w/v), 7% (w/v), 7.5% (w/v), 8% (w/v), 8.5% (w/v), 9% (w/v), 9.5% (w/v), or 10% (w/v), or any concentration in between.

In some embodiments, a pharmaceutical composition for use in the invention comprises polysorbate 20 (PS20) and/or polysorbate 80 (PS80) at a concentration of 0.01% (w/v) to 0.1% (w/v) or 0.02% (w/v) to 0.08% (w/v). For example, the concentration of polysorbate 20 and/or polysorbate 80 can be 0.01%, 0.02%, 0.03%, 0.04%, 0.05%, 0.06%, 0.07%, 0.08%, 0.09% or 0.1% (w/v), or any concentration in between.

In some embodiments, a pharmaceutical composition for use in the invention comprises lactic acid, sodium lactate, acetic acid or sodium acetate at a concentration of 10 mM to 20 mM based on the amount of lactate or acetate, respectively. For example, the concentration of lactate or acetate can be 10 mM, 11 mM, 12 mM, 13 mM, 14 mM, 15 mM, 16 mM, 17 mM, 18 mM, 19 mM, 20 mM, or any concentration in between.

Pharmaceutical compositions comprising an anti-IFN-α/-ω antibody for use in the invention can be prepared by any method known in the art in view of the present disclosure. For example, an anti-IFN-α/-ω antibody can be mixed with one or more pharmaceutically acceptable carriers to obtain a solution. The solution can be stored as a frozen liquid at a controlled temperature ranging from −40° C.±10° C. to −70° C.±20° C. and under protection from light exposure in an appropriate vial until administered to the subject.

According to embodiments of the invention, a variety of factors can be analyzed to determine by clinical trials such as those described herein whether a particular dosage of the anti-IFN-α/-ω antibody provides for safe subcutaneous and/or intravenous administration. For example, safety of a certain dosage of subcutaneously and/or intravenously administered anti-IFN-α/-ω antibody can be assessed by immunogenicity studies (e.g., measuring the production of antibodies to the anti-IFN-α/-ω antibody); by pharmacokinetic studies (e.g., an area under the concentration time curve (AUC), and a maximum concentration observed ($C_{max}$). The safety of subcutaneously and/or intravenously administered anti-IFN-α/-ω antibody can also be monitored by physical examination of the subject; observation of local injection site reactions, systemic injection related reactions, and other allergic reactions; electrocardiograms; clinical laboratory tests; vital signs; and monitoring of other adverse events, such as thromboembolic events.

In some embodiments, clinically proven safe administration of an anti-IFN-α/-ω antibody and/or clinically proven safe treatment of an autoimmune disease is determined by measuring amounts of antibodies to the administered anti-IFN-α/-ω antibody in a sample obtained from a subject. The amounts of antibodies to the anti-IFN-α/-ω antibody can be measured by any method known in the art in view of the present disclosure, e.g., ELISA.

In some embodiments, clinically proven safe administration of an anti-IFN-α/-ω antibody and/or clinically proven safe treatment of an IFN-mediated disease is determined by assessing pharmacokinetic (PK) parameters, such as an area under the concentration time curve (AUC), and a maximum concentration observed ($C_{max}$), of the anti-IFN-α/-ω antibody in the serum of the subject. Serum samples are analyzed to determine concentrations of the anti-IFN-α/-ω antibody by any method known in the art in view of the present disclosure. The pharmacokinetic parameters are then analyzed, for example by non-compartment analysis (NCA), to calculate pharmacokinetic parameters, such as AUC, $C_{max}$, terminal half-life ($T_{1/2}$), total systemic clearance after intravenous administration (CL), volume of distribution at terminal phase ($V_z$), total systemic clearance over bioavailability (CL/F), and volume of distribution at terminal phase over bioavailability ($V_z$/F).

In some embodiments, clinically proven safe administration of an anti-IFN-α/-ω antibody achieves $AUC_{(0-t)}$ (AUC versus time curve from time 0 to the time corresponding to the last quantifiable serum concentration) about 50 μg·day/mL to about 7000 μg·day/mL. For example, the $AUC_{(0-t)}$ can be 50 μg·day/mL, 100 μg·day/mL, 500 μg·day/mL, 1000 μg·day/mL, 2000 μg·day/mL, 3000 μg·day/mL, 4000 μg·day/mL, 5000 μg·day/mL, 6000 μg·day/mL, 7000 μg·day/mL, or any number in between.

In some embodiments, clinically proven safe administration of an anti-IFN-α/-ω antibody achieves a maximum concentration observed ($C_{max}$) of about 5 μg/mL to about 500 μg/mL. For example, the $C_{max}$ can be about 5 μg/mL, 10 μg/mL, 50 μg/mL, 100 μg/mL, 200 μg/mL, 300 μg/mL, 400 μg/mL, 500 μg/mL, or any number in between.

In some embodiments, clinically proven safe treatment of an IFN-I mediated disease with administration of an anti-IFN-α/-ω antibody achieves $AUC_{(0-t)}$ (AUC versus time curve from time 0 to the time corresponding to the last quantifiable serum concentration) about 1000 μg·day/mL to about 3500 μg·day/mL. For example, the $AUC_{(0-t)}$ can be 1000 μg·day/mL, 1500 μg·day/mL, 2000 μg·day/mL, 2500 μg·day/mL, 3000 μg·day/mL, 3500 μg·day/mL, or any number in between.

In some embodiments, clinically proven safe treatment of an IFN-mediated disease with administration of an anti-IFN-α/-ω antibody achieves a maximum concentration observed ($C_{max}$) of about 120 μg/mL to about 400 μg/mL. For example, the $C_{max}$ can be about 120 μg/mL, 150 g/mL, 200 μg/mL, 250 μg/mL, 300 μg/mL, 350 μg/mL, 400 μg/mL, or any number in between.

In another general aspect, the method of the invention further comprises a method of diagnosing a subject having an IFN-I mediated disease that is responsive to treatment of an anti-IFN-α-/ω antibody, comprising:

a. assaying gene expression of one or more genes DHX58, EIF2AK2, HERC5, IFI44, IFI44L, IFI6, IRF7, PARP9, PLSCR1 and SAMD9L in a biological sample of the human subject; and b. identifying the human subject as responsive to treatment of the antibody prior to administering to the subject the pharmaceutical composition comprising the antibody and the pharmaceutically acceptable carrier.

In particular, this diagnosing method is further described in, e.g., U.S. Provisional Patent Application No. 62/751,019, the contents of which are herein incorporated by reference in their entireties.

Embodiments

The invention provides also the following non-limiting embodiments.

Embodiment 1 is a method of administration of an anti-IFN-α/-ω antibody or antigen binding fragment thereof to a human subject in need thereof in a clinically proven safe amount, comprising subcutaneously or intravenously administering to the human subject a pharmaceutical composition comprising the antibody and a pharmaceutically acceptable carrier, wherein a total dosage of the antibody administered is 0.1 mg/kg to 20 mg/kg body weight of the subject per administration.

Embodiment 1a is the method of embodiment 1, wherein the anti-IFN-α/-ω antibody comprises a heavy chain variable region and a light chain variable region, the heavy chain variable region comprising heavy chain complementarity determining regions (HCDRs) HCDR1, HCDR2 and HCDR3 amino acid sequences of SEQ ID NOs: 33, 34, and 35, respectively, and the light chain variable region comprising light chain complementarity determining regions (LCDRs) LCDR1, LCDR2 and LCDR3 amino acid sequences of SEQ ID NOs: 30, 31, and 32, respectively.

Embodiment 1b is the method of embodiment 1 or 1a, wherein the anti-IFN-α/-ω antibody comprises a heavy chain variable region (VH) having the amino acid sequence of SEQ ID NO: 28 and a light chain variable region (VL) having the amino acid sequences of SEQ ID NO: 29.

Embodiment 1c is the method of embodiment 1, wherein the anti-IFN-α/-ω antibody is IFWM3405, IFWM3442, IFWM3525, IFWM3423, IFWM3444 or IFWM3421 described in U.S. Pat. No. 10,208,113, the content of which is herein incorporated by reference in its entirety.

Embodiment 1d is the method of any one of embodiments 1 to c, wherein the anti-IFN-α/-ω antibody is a fully human antibody.

Embodiment 2 is the method of any of embodiments 1-d, wherein the pharmaceutical composition is administered intravenously.

Embodiment 2a is the method of embodiment 2, wherein the total dosage of the anti-IFN-α/-ω antibody administered per administration is 0.1 mg/kg, 0.3 mg/kg, 1 mg/kg, 3 mg/kg, 10 mg/kg, 15 mg/kg or 20 mg/kg body weight of the subject, or any dosage in between.

Embodiment 2b is the method of embodiment 2 or 2a, wherein the pharmaceutical composition is administered to the human subject intravenously for no less than 30 minutes.

Embodiment 3 is the method of any of embodiments 1-d, wherein the pharmaceutical composition is administered subcutaneously.

Embodiment 3a is the method of embodiment 3, wherein the total dosage of the anti-IFN-α/-ω antibody administered per administration is 0.1 mg/kg, 0.3 mg/kg, 0.5 mg/kg, 0.7 mg/kg, 1 mg/kg, 1.2 mg/kg, 1.5 mg/kg, 1.7 mg/kg, 2 mg/kg, 2.3 mg/kg or 2.5 mg/kg body weight of the subject, or any dosage in between.

Embodiment 4 is the method of any one of embodiments 1-3a, wherein the administration of the pharmaceutical composition achieves, in the plasma of the subject, at least one parameter selected from: (i) an area under the concentration time curve $(AUC)_{(0-t)}$ of about 50 μg·day/mL to about 7000 μg·day/mL, and (ii) a maximum concentration observed ($C_{max}$) of about 5 μg/mL to about 500 μg/mL.

Embodiment 4a is the method of embodiment 4, wherein the administration of the pharmaceutical composition achieves, in the plasma of the subject, an area under the concentration time curve $(AUC)_{(0-t)}$ of about 50 μg·day/mL, 100 μg·day/mL, 500 μg·day/mL, 1000 μg·day/mL, 2000 μg·day/mL, 3000 μg·day/mL, 4000 μg·day/mL, 5000 μg·day/mL, 6000 μg·day/mL, 7000 μg·day/mL, or any number in between.

Embodiment 4a is the method of embodiment 4, wherein the human subject is a healthy subject, and the intravenous administration of a single dose of 0.3 mg/kg, 1.0 mg/kg, 3.0 mg/kg, 10 mg/kg or 15 mg/kg of the anti-IFN-α/-ω antibody achieves, in the plasma of the subject, an area under the concentration time curve $(AUC)_{(0-t)}$ of 88.8 (126), 287 (31.9), 1143 (245), 3694 (610), or 5944 (1036) μg·day/mL, respectively.

Embodiment 4b is the method of embodiment 4 or 4a, wherein the human subject is a healthy subject, and the intravenous administration of a single dose of 0.3 mg/kg, 1.0 mg/kg, 3.0 mg/kg, 10 mg/kg or 15 mg/kg of the anti-IFN-α/-ω antibody achieves, in the plasma of the subject, a maximum concentration observed ($C_{max}$) of 7.14 (0.961), 22.5 (2.21), 76.5 (9.30), 230 (22.4), or 403 (65.7) g/mL, respectively.

Embodiment 4c is the method of embodiment 4, wherein the human subject is a healthy subject, and the subcutaneous administration of a single dose of 1.0 mg/kg of the anti-IFN-α/-ω antibody achieves, in the plasma of the subject, an area under the concentration time curve $(AUC)_{(0-t)}$ of 226 (69.5) μg·day/mL.

Embodiment 4d is the method of embodiment 4 or 4c, wherein the human subject is a healthy subject, and the subcutaneous administration of a single dose of 1.0 mg/kg of the anti-IFN-α/-ω antibody achieves, in the plasma of the subject, a maximum concentration observed ($C_{max}$) of 7.96 (2.48) g/mL.

Embodiment 5 is the method of any one of embodiments 1-4d, wherein the administration of the anti-IFN-α/-ω antibody does not result in production of antibodies against the anti-IFN-α/-ω antibody in the subject.

Embodiment 6 is the method of any of embodiments 1-5, wherein the human subject is in need of a treatment of an IFN-I mediated disease, such as systemic lupus erythematosus (SLE), type I diabetes, psoriasis, primary Sjögren's disease, systemic sclerosis, rheumatoid arthritis, transplant rejection, dermatomyositis, polymyositis, Aicardi-Goutieres syndrome, Sting associated vasculopathy with onset in infancy (SAVI) or chronic atypical neutrophilic dermatosis with lipodystrophy and elevated temperature syndrome (CANDLE).

Embodiment 7 is the method of embodiment 6, wherein the human subject is in need of a treatment of mild to moderate systemic lupus erythematosus (SLE).

Embodiment 8 is the method of any one of embodiments 6-7, wherein the pharmaceutical composition is administered to the human subject intravenously.

Embodiment 8a is the method of embodiment 8, wherein a total dosage of the anti-IFN-α/-ω antibody administered is 10 mg/kg body weight of the subject per administration.

Embodiment 8b is the method of embodiment 8 or 8a, wherein the pharmaceutical composition is administered to the human subject once every two weeks.

Embodiment 9 is the method of any one of embodiments 6-7, wherein the pharmaceutical composition is administered to the human subject subcutaneously.

Embodiment 9a is the embodiment 9, wherein a total dosage of the anti-IFN-α/-ω antibody administered is 1 mg/kg body weight of the subject per administration.

Embodiment 10 is the method of any one of embodiments 7-9a, wherein the administration of the pharmaceutical composition achieves, in the plasma of the subject, at least one parameter selected from: (i) an area under the concentration time curve $(AUC)_{(0-14d)}$ of about 800 μg·day/mL to about 3500 μg·day/mL, and (ii) a maximum concentration observed ($C_{max}$) of about 100 μg/mL to about 400 μg/mL.

Embodiment 10a is the method of embodiment 10, wherein the pharmaceutical composition is intravenously administered to the human subject once every two weeks at 10 mg/kg of the anti-IFN-α/-ω antibody per administration, and after the first dose, the administration achieves, in the plasma of the subject, an area under the concentration time curve during a dosing interval $(AUC)_{(0-14d)}$ of 1387 (354) μg·day/mL.

Embodiment 10b is the method of embodiment 10 or 10a, wherein the pharmaceutical composition is intravenously administered to the human subject once every two weeks at 10 mg/kg of the anti-IFN-α/-ω antibody per administration, and after the sixth dose, the administration achieves, in the plasma of the subject, an area under the concentration time curve during a dosing interval $(AUC)_{(0-14d)}$ of 2340 (690) μg·day/mL.

Embodiment 10c is the method of any one of embodiments 10 to 10b, wherein the intravenous administration of a first dose of 10 mg/kg of the anti-IFN-α/-ω antibody achieves, in the plasma of the subject, a maximum concentration observed ($C_{max}$) of 194 (46.3).

Embodiment 10d is the method of any one of embodiments 10 to 10c, wherein the intravenous administration of a sixth dose of 10 mg/kg of the anti-IFN-α/-ω antibody achieves, in the plasma of the subject, a maximum concentration observed ($C_{max}$) of 289 (72.6), wherein each dose of the pharmaceutical composition is administered to the human subject once every two weeks.

Embodiment 11 is the method of any one of embodiments 7-10d, wherein the human subject has a reduction in the Systemic Lupus Erythematosus Responder Index (SRI), preferably a reduction of 4 points, more preferably 5 points, and most preferably 6 points, by day 100 after the administration of the pharmaceutical composition.

Embodiment 12 is the method of any one of embodiments 7-11, wherein the human subject has no new British Isles Lupus Assessment Group (BILAG) A or 2B shifts by day 100 after the administration of the pharmaceutical composition.

Embodiment 13 is the method of any one of embodiments 7-12, wherein the human subject has a reduction in the Systemic Lupus Erythematosus Disease Activity Index 2000 (SLEDAI-2K) from baseline by day 100 after the administration of the pharmaceutical composition.

Embodiment 14 is the method of any one of embodiments 7-13, wherein the human subject has a reduction in the Systemic Lupus Erythematosus 2000 Responder Index-50 (S2K RI-50) from baseline by day 100 after the administration of the pharmaceutical composition.

Embodiment 15 is the method of any one of embodiments 7-14, wherein the human subject has a reduction in the Physician's Global Assessment of Disease Activity (PGA) from baseline by day 100 after the administration of the pharmaceutical composition.

Embodiment 16 is the method of any one of embodiments 6-15, wherein the human subject achieves a steady-state condition of the antibody within 40-50 days after administration.

Embodiment 17 is the method of any one of embodiments 6-16, wherein the administration of the anti-IFN-α/-ω antibody does not result in a treatment emergent adverse event (TEAE) related to a malignancy or anaphylactic or serum sickness-type reaction in the subject.

Embodiment 18 is a method of providing clinically proven safe treatment of an IFN-I mediated disease in a human subject in need thereof, the method comprising subcutaneously or intravenously administering to the subject a pharmaceutical composition comprising an anti-IFN-α/-ω antibody and a pharmaceutically acceptable carrier, wherein a total dosage of the anti-IFN-α/-ω antibody administered is 0.1 mg/kg to 20 mg/kg body weight of the subject per administration.

Embodiment 18a is the method of embodiment 18, wherein the anti-IFN-α/-ω antibody comprises a heavy chain variable region and a light chain variable region, the heavy chain variable region comprising heavy chain complementarity determining regions (HCDRs) HCDR1, HCDR2 and HCDR3 amino acid sequences of SEQ ID NOs: 33, 34, and 35, respectively, and the light chain variable region comprising light chain complementarity determining regions (LCDRs) LCDR1, LCDR2 and LCDR3 amino acid sequences of SEQ ID NOs: 30, 31, and 32, respectively.

Embodiment 18b is the method of embodiment 18 or 18a, wherein the anti-IFN-α/-ω antibody comprises a heavy chain variable region (VH) having the amino acid sequence of SEQ ID NO: 28 and a light chain variable region (VL) having the amino acid sequences of SEQ ID NO: 29.

Embodiment 18c is the method of embodiment 18, wherein the anti-IFN-α/-ω antibody is IFWM3405, IFWM3442, IFWM3525, IFWM3423, IFWM3444 or IFWM3421 described in U.S. Pat. No. 10,208,113, the content of which is herein incorporated by reference in its entirety.

Embodiment 18d is the method of any one of embodiments 18 to 18c, wherein the anti-IFN-α/-ω antibody is a fully human antibody.

Embodiment 19 is the method of any of embodiments 18-18d, wherein the IFN-I mediated disease is selected from the group consisting of systemic lupus erythematosus (SLE), type I diabetes, psoriasis, primary Sjögren's disease, systemic sclerosis, rheumatoid arthritis, transplant rejection, dermatomyositis, polymyositis, Aicardi-Goutieres syndrome, Sting associated vasculopathy with onset in infancy (SAVI) or chronic atypical neutrophilic dermatosis with lipodystrophy and elevated temperature syndrome (CANDLE).

Embodiment 20 is the method of embodiment 19, wherein the human subject is in need of a treatment of mild to moderate systemic lupus erythematosus (SLE).

Embodiment 21 is the method of any one of embodiments 18-20, wherein the pharmaceutical composition is administered to the human subject intravenously for no less than 30 minutes.

Embodiment 21a is the method of embodiment 21, wherein a total dosage of the anti-IFN-α/-ω antibody administered is 10 mg/kg body weight of the subject per administration.

Embodiment 21b is the method of embodiment 21a, wherein the pharmaceutical composition is administered to the human subject once every two weeks.

Embodiment 22 is the method of any one of embodiments 18-20, wherein the pharmaceutical composition is administered to the human subject subcutaneously.

Embodiment 22a is the embodiment 22, wherein a total dosage of the anti-IFN-α/-ω antibody administered is 1 mg/kg body weight of the subject per administration.

Embodiment 23 is the method of any one of embodiments 18-22a, wherein the administration of the anti-IFN-α/-ω antibody does not result in production of antibodies against the anti-IFN-α/-ω antibody in the subject.

Embodiment 24 is the method of any one of embodiments 18-23, wherein the administration of the pharmaceutical composition achieves, in the plasma of the subject, at least one parameter selected from: (i) an area under the concentration time curve $(AUC)_{(0-t)}$ of about 50 μg·day/mL to about 7000 μg·day/mL, and (ii) a maximum concentration observed ($C_{max}$) of about 5 μg/mL to about 500 μg/mL.

Embodiment 24a is the method of embodiment 24, wherein the administration of the pharmaceutical composition achieves, in the plasma of the subject, at least one parameter selected from: (i) an area under the concentration time curve $(AUC)_{(0-14d)}$ of about 800 μg·day/mL to about 3500 μg·day/mL, and (ii) a maximum concentration observed ($C_{max}$) of about 100 μg/mL to about 400 μg/mL.

Embodiment 24b is the method of embodiment 24a, wherein the pharmaceutical composition is intravenously administered to the human subject once every two weeks at 10 mg/kg of the anti-IFN-α/-ω antibody per administration, and after the first dose, the administration achieves, in the plasma of the subject, an area under the concentration time curve during a dosing interval $(AUC)_{(0-14d)}$ of 1387 (354) μg·day/mL.

Embodiment 24c is the method of embodiment 24a or 24b, wherein the pharmaceutical composition is intravenously administered to the human subject once every two weeks at 10 mg/kg of the anti-IFN-α/-ω antibody per administration, and after the sixth dose, the administration achieves, in the plasma of the subject, an area under the concentration time curve during a dosing interval $(AUC)_{(0-14d)}$ of 2340 (690) μg·day/mL.

Embodiment 24d is the method of any one of embodiments 24a to 24c, wherein the intravenous administration of a first dose of 10 ng/kg of the anti-IFN-α/-ω antibody achieves, in the plasma of the subject, a maximum concentration observed ($C_{max}$) of 194 (46.3).

Embodiment 24e is the method of any one of embodiments 24a to 24d, wherein the intravenous administration of a sixth dose of 10 mg/kg of the anti-IFN-α/-ω antibody achieves, in the plasma of the subject, a maximum concentration observed ($C_{max}$) of 289 (72.6), wherein each dose of the pharmaceutical composition is administered to the human subject once every two weeks.

Embodiment 25 is the method of any one of embodiments 18-24e, wherein the human subject has a reduction in the Systemic Lupus Erythematosus Responder Index (SRI), preferably a reduction of 4 points, more preferably 5 points, and most preferably 6 points, by day 100 after the administration of the pharmaceutical composition.

Embodiment 26 is the method of any one of embodiments 18-25, wherein the human subject has no new British Isles Lupus Assessment Group (BILAG) A or 2B shifts by day 100 after the administration of the pharmaceutical composition.

Embodiment 27 is the method of any one of embodiments 18-26, wherein the human subject has a reduction in the Systemic Lupus Erythematosus Disease Activity Index 2000 (SLEDAI-2K) from baseline by day 100 after the administration of the pharmaceutical composition.

Embodiment 28 is the method of any one of embodiments 18-27, wherein the human subject has a reduction in the Systemic Lupus Erythematosus 2000 Responder Index-50 (S2K RI-50) from baseline by day 100 after the administration of the pharmaceutical composition.

Embodiment 29 is the method of any one of embodiments 18-28, wherein the human subject has a reduction in the Physician's Global Assessment of Disease Activity (PGA) from baseline by day 100 after the administration of the pharmaceutical composition.

Embodiment 30 is the method of any one of embodiments 18-29, wherein the human subject achieves a steady-state condition of the antibody within 40-50 days after administration.

Embodiment 31 is the method of any one of embodiments 18-30, wherein the administration of the anti-IFN-α/-ω antibody does not result in a treatment emergent adverse event (TEAE) related to a malignancy or anaphylactic or serum sickness-type reaction in the subject.

Embodiment 32 is the method of any one of embodiments 1-31, further comprising:
   a. providing a biological sample from the human subject;
   b. assaying gene expression of one or more genes DHX58, EIF2AK2, HERC5, IFI44, IFI44L, IFI6, IRF7, PARP9, PLSCR1 and SAMD9L in a biological sample of the human subject; and
   c. identifying the human subject as responsive to treatment of the antibody prior to administering to the subject the pharmaceutical composition comprising the antibody and the pharmaceutically acceptable carrier.

Embodiment 33 is the method of embodiment 32, comprising:
   a. providing a biological sample from the human subject;
   b. assaying gene expression of genes DHX58, EIF2AK2, HERC5, IFI44, IFI44L, IFI6, IRF7, PARP9, PLSCR1 and SAMD9L in a biological sample of the human subject;
   c. determining a combined expression value of the genes DHX58, EIF2AK2, HERC5, IFI44, IFI44L, IFI6, IRF7, PARP9, PLSCR1 and SAMD9L in the biological sample; and
   d. identifying the human subject as responsive to treatment of the antibody prior to administering to the subject the pharmaceutical composition comprising the antibody and the pharmaceutically acceptable carrier.

Embodiment 34 is the method of embodiment 33, comprising:
   a. providing a biological sample from the human subject;
   b. assaying gene expression of genes DHX58, EIF2AK2, HERC5, IFI44, IFI44L, IFI6, IRF7, PARP9, PLSCR1 and SAMD9L in a biological sample of the human subject;
   c. determining a combined expression value of the genes DHX58, EIF2AK2, HERC5, IFI44, IFI44L, IFI6, IRF7, PARP9, PLSCR1 and SAMD9L in the biological sample;
   d. determining that the human subject has an elevated IFN-I signature when the combined expression value is equal to or higher than a threshold value; and
   b. identifying the human subject as responsive to treatment of the antibody prior to administering to the subject the pharmaceutical composition comprising the antibody and the pharmaceutically acceptable carrier.

Embodiment 35 is the method of any one of embodiments 1 to 34, wherein the pharmaceutical composition comprises the anti-IFN-α/-ω antibody at a concentration of 1 mg/mL to 100 mg/mL, and a pharmaceutically acceptable carrier.

Embodiment 35a is the method of embodiment 35, wherein the concentration of the anti-IFN-α/-ω antibody is 1 mg/mL, 10 mg/mL, 20 mg/mL, 30 mg/mL, 40 mg/mL, 50 mg/mL, 60 mg/mL, 70 mg/mL, 80 mg/mL, 90 mg/mL, or 100 mg/mL, or any concentration in between.

Embodiment 35b is the method of embodiment 35 or 35a, wherein the pharmaceutically acceptable carrier comprises one or more carbohydrates, such as lactose, maltose, sucrose, at a concentration of 1% to 10% weight by volume (w/v), such as 5% to 10% (w/v).

Embodiment 35c is the method of embodiment 35b, wherein the pharmaceutically acceptable carrier comprises at least one of lactose, maltose and sucrose, at a concentration of 1% (w/v), 1.5% (w/v), 2% (w/v), 2.5% (w/v), 3% (w/v), 3.5% (w/v), 4% (w/v), 4.5% (w/v), 5% (w/v), 5.5% (w/v), 6% (w/v), 6.5% (w/v), 7% (w/v), 7.5% (w/v), 8% (w/v), 8.5% (w/v), 9% (w/v), 9.5% (w/v), or 10% (w/v), or any concentration in between.

Embodiment 35d is the method of any one of embodiments 35 to 35c, wherein the pharmaceutically acceptable carrier comprises one or more surfactants, such as polysorbate 20, polysorbate 80 at a concentration of 0.01% (w/v) to 0.1% (w/v) or 0.02% (w/v) to 0.08% (w/v).

Embodiment 35e is the method of embodiment 35d, wherein the pharmaceutically acceptable carrier comprises at least one of polysorbate 20 and polysorbate 80 at a concentration of 0.01%, 0.02%, 0.03%, 0.04%, 0.05%, 0.06%, 0.07%, 0.08%, 0.09% or 0.1% (w/v), or any concentration in between.

Embodiment 35f is the method of any one of embodiments 35 to 35e, wherein the pharmaceutically acceptable carrier comprises one or more acids and/or salts, such as lactic acid, sodium lactate, acetic acid, sodium acetate at a concentration of 10 mM to 20 mM based on the amount of lactate or acetate, respectively.

Embodiment 35g is the method of embodiment 35f, wherein the pharmaceutically acceptable carrier comprises at least one of sodium lactate and sodium acetate at a concentration of 10 mM, 11 mM, 12 mM, 13 mM, 14 mM, 15 mM, 16 mM, 17 mM, 18 mM, 19 mM, 20 mM, or any concentration in between.

Embodiment 35h is the method of any one of embodiments 35 to 35g, wherein the pharmaceutical composition has a pH of 5.0-6.0, such as a pH of 5.0, 5.1, 5.2, 5.3, 5.4, 5.5, 5.6, 5.7, 5.8, 5.9, 6.0, or any value in between.

Embodiment 36 is the method of any one of embodiments 1 to 34, wherein the pharmaceutical comprises 20 mg/mL to 80 mg/mL of the anti-IFN-α/-ω antibody and a pharmaceutically acceptable carrier.

Embodiment 36a is the method of embodiment 36, wherein the pharmaceutically acceptable carrier comprises 1 mM to 20 mM acetate.

Embodiment 36b is the method of embodiment 36, wherein the pharmaceutically acceptable carrier comprises 1 mM to 20 mM lactate.

Embodiment 36c is the method of any one of embodiments 36 to 36b, wherein the pharmaceutically acceptable carrier comprises 5% to 10% (w/v) lactose.

Embodiment 36d is the method of any one of embodiments 36 to 36b, wherein the pharmaceutically acceptable carrier comprises 5% to 10% (w/v) maltose.

Embodiment 36e is the method of any one of embodiments 36 to 36b, wherein the pharmaceutically acceptable carrier comprises 5% to 10% (w/v) sucrose.

Embodiment 36f is the method of any one of embodiments 36 to 36e, wherein the pharmaceutically acceptable carrier comprises 0.01% to 0.10% (w/v) polysorbate 20 (PS20).

Embodiment 36g is the method of any one of embodiments 36 to 36e, wherein the pharmaceutically acceptable carrier comprises 0.01% to 0.10% (w/v) polysorbate 80 (PS80).

Embodiment 36h is the method of any one of embodiments 36 to 36g, wherein the pharmaceutical composition has a pH of 5.0-6.0, such as a pH of 5.0, 5.1, 5.2, 5.3, 5.4, 5.5, 5.6, 5.7, 5.8, 5.9, 6.0, or any value in between.

Embodiment 37 is the method of any one of embodiments 1 to 34, wherein the pharmaceutical comprises 30 mg/mL of the anti-IFN-α/-ω antibody, 5 mM lactate, 5% (w/v) lactose, and 0.02% (w/v) polysorbate 80 (PS80), at pH 5.5.

Embodiment 38 is the method of any one of embodiments 1 to 34, wherein the pharmaceutical comprises 40 mg/mL of the anti-IFN-α/-ω antibody, 8 mM acetate, 8% (w/v) maltose, and 0.06% (w/v) polysorbate 20 (PS20), at pH 5.0.

Embodiment 39 is the method of any one of embodiments 1 to 34, wherein the pharmaceutical composition comprises 50 mg/mL of the anti-IFN-α/-ω antibody, 13 mM acetate, 8.0% (w/v) sucrose, and 0.04% (w/v) polysorbate 20 (PS20), at pH 5.2.

Embodiment 40 is the method of any one of embodiments 1 to 34, wherein the pharmaceutical comprises 60 mg/mL of the anti-IFN-α/-ω antibody, 10 mM acetate, 8% (w/v) lactose, and 0.06% (w/v) polysorbate 20 (PS20), at pH 5.4.

Embodiment 41 is the method of any one of embodiments 1 to 34, wherein the pharmaceutical comprises 70 mg/mL of the anti-IFN-α/-ω antibody, 15 mM lactate, 10% (w/v) maltose, and 0.06% (w/v) polysorbate 80 (PS80), at pH 5.0.

Having generally described the invention, the same will be more readily understood by reference to the following Examples, which are provided by way of illustration and are not intended as limiting. Further details of the invention are illustrated by the following non-limiting Examples. The disclosures of all citations in the specification are expressly incorporated herein by reference.

EXAMPLES

Example: A Phase 1, Randomized, Double-Blind, Placebo-Controlled, Single Ascending Dose Study in Healthy Subjects and Multiple Dose Study of ANTIBODY A in Subjects with Mild to Moderate Systemic Lupus Erythematosus This clinical study was the first administration of a fully human anti-IFN-α/-ω antibody ("ANTIBODY A") in human. The antibody A has a heavy chain variable region (VH) amino acid sequence of SEQ ID NO: 28 and a light chain variable region (VL) amino acid sequences of SEQ ID NO: 29 and is an IgG1κ. The purpose of this study was to assess the safety and tolerability of ANTIBODY A through single ascending intravenous (IV) dose administration and a single subcutaneous (SC) dose in healthy subjects (Part A) and multiple IV dose administrations in subjects with mild to moderate systemic lupus erythematosus (SLE) (Part B).

Objectives
Primary Objectives
1) Assess the safety and tolerability of ANTIBODY A following single ascending IV dose administration in healthy subjects and a single SC dose of 1 mg/kg in healthy subjects (Part A);
2) Assess the safety and tolerability of ANTIBODY A following multiple IV dose administrations in subjects with mild to moderate SLE (Part B).

Secondary Objectives
1) Assess the PK and immunogenicity of ANTIBODY A following single ascending IV dose administration in healthy subjects and a single SC dose of 1 mg/kg in healthy subjects (Part A), and following multiple IV dose administrations in subjects with mild to moderate SLE (Part B);
2) Evaluate pharmacodynamic (PD) effects and clinical responses following a single IV or SC dose of ANTIBODY A in healthy subjects (Part A), and evaluate PD and clinical response following multiple IV doses of ANTIBODY A in subjects with mild to moderate SLE (Part B).

Exploratory Objectives
1) Evaluate biomarkers following a single IV or SC dose of ANTIBODY A in healthy subjects (Part A), and following multiple IV doses of ANTIBODY A in subjects with mild to moderate SLE (Part B);

2) Evaluate the level of dysregulation of IFN signaling and how this dysregulation correlates with changes in other biomarkers and clinical response measures to administration of study agent;
3) Explore the variability of IFN signatures across different racial/ethnic populations and its potential impact on clinical response associated with exposure to study agent;
4) Explore PK/PD relationships of ANTIBODY A through analysis of biomarkers, PD markers, and clinical response.

Methods and Subjects
Overview of Study Design

Part A of the study assessed the safety, tolerability, PK, and immunogenicity of a single administration of ANTIBODY A or placebo in healthy subjects with no confounding significant medical problems or chronic medications, where frequent PK sampling was obtained, and biomarkers and PD were also assessed. Single ascending IV doses of 0.3 mg/kg, 1.0 mg/kg, 3.0 mg/kg, 10.0 mg/kg, or 15.0 mg/kg of ANTIBODY A or placebo were administered to sequential cohorts of healthy subjects as an IV infusion of at least 30 minutes. An additional cohort received a single 1 mg/kg SC administration of ANTIBODY A.

Part B of the study, in subjects with mild to moderate SLE, explored clinical response, safety, and tolerability as well as assessed impact on biomarkers such as the target engagement (total and free IFN), IFN-related RNA expression signature, and associated proteins over time. Additional investigation of incremental effect on biomarker readouts were performed to assess variability in the ability to attenuate IFN-mediated signaling across different racial/ethnic populations. If appropriate, subgroup analyses of clinical response and safety parameters were to be performed to evaluate variability and explore the effects of treatment across different subpopulations. In Part B, 6 doses of 10 mg/kg ANTIBODY A or placebo were administered every 2 weeks as an IV infusion of at least 30 minutes. Randomization was stratified by racial/ethnic subpopulation (Asian/non-Asian) and elevated level of serologic disease activity (present/absent).

The duration of subject participation was approximately 13 weeks for healthy subjects and 22 weeks for SLE subjects, including a screening visit up to 28 days prior to study agent administration. The healthy subjects had a 6-day/5-night inpatient period. All subjects received study agent on day 1 and SLE subjects received additional doses on Days 15, 29, 43, 57, and 71.

A diagram of the study design is provided in FIG. 1.
Study Agent

ANTIBODY A is supplied as a frozen, preservative-free, final liquid-in-vial (LIV) presentation suitable for IV and SC administration.

Subjects

Figure 2:
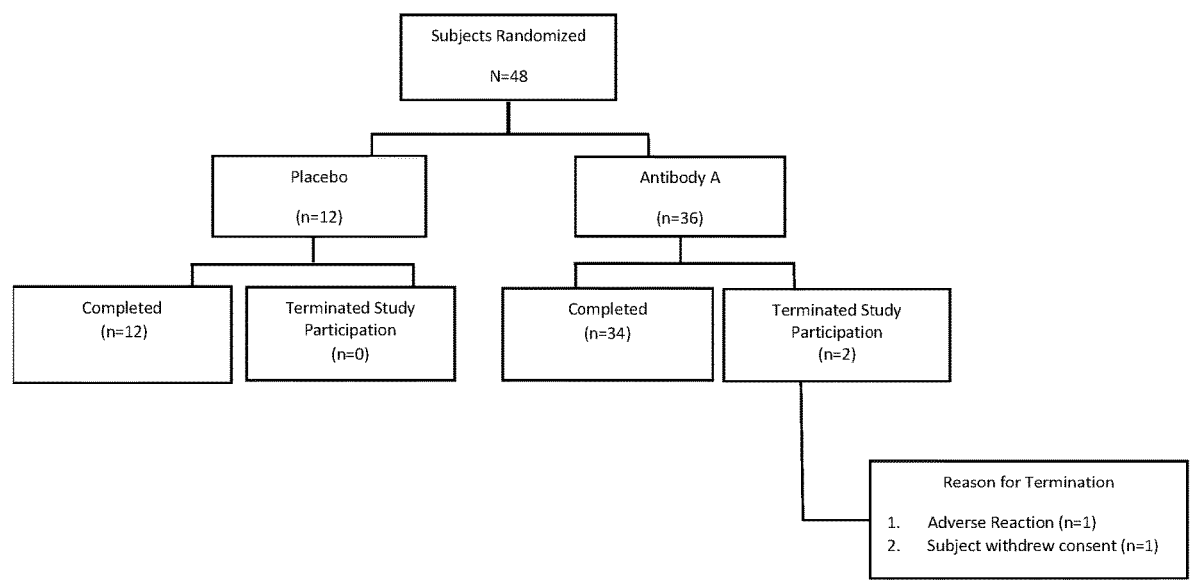
FIG. 2 shows the disposition of subjects in Part A of the study.

Part A: A total of 48 healthy adult subjects (40 male; 8 female) without no confounding significant medical problems or chronic medications were enrolled. 30 subjects received single ascending IV doses (0.3 to 15.0 mg/kg) of ANTIBODY A, 6 subjects received SC doses (1.0 mg/kg), and 12 subjects received placebo. Two subjects from the ANTIBODY A group did not complete the study. FIG. 2 represents the disposition of subjects in Part A.

Part B: Subjects eligible for enrollment had to meet the following key criteria:
3) Must meet Systemic Lupus International Collaborating Clinics (SLICC) criteria for diagnosis of lupus with at least 1 Systemic Lupus Erythematosus Disease Activity Index 2000 (SLEDAI-2K)-defined non-serologic clinical activity within 3 months prior to first dose of study agent.
4) In addition to meeting SLICC criteria, must be serologically defined as positive within 2 months prior to, or at screening:
e) a positive anti-nuclear antibody (ANA) titer of ≥1:80, or
f) a positive anti-double stranded deoxyribonucleic acid test (note: if Anti-dsDNA is done
by enzyme-linked immunosorbent assay, a test 2× upper limit of normal is required to be considered unequivocally positive) or
g) a positive anti-Smith antibody and/or positive anti-ribonucleoprotein (RNP) antibody and/or anti-Ro antibody, and in addition to at least one of the above:
h) a positive lupus IFN profile score during screening (prior to randomization).

Figure 3:
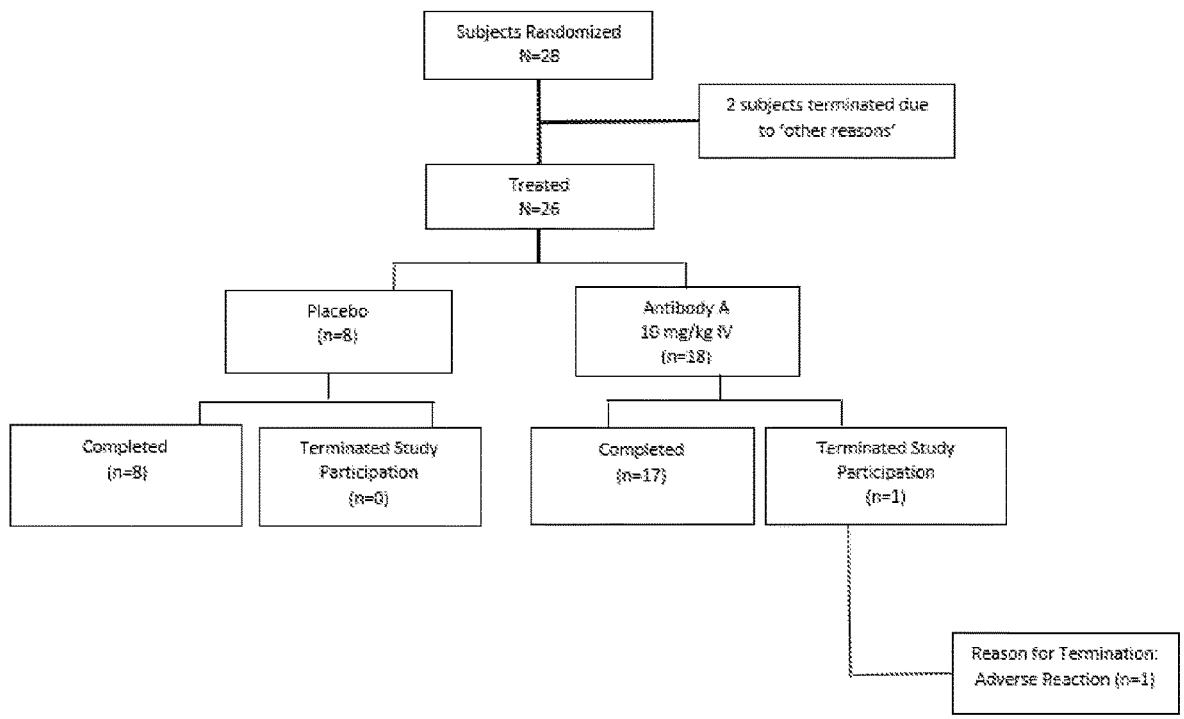
FIG. 3 shows the disposition of subjects in Part B of the study.

A total of 28 subjects (27 females: 1 male) with mild to moderate SLE were randomized in Part B (20 subjects: 10 mg/kg IV dose; 8 subjects: placebo). Three subjects from the ANTIBODY A group did not complete the study. FIG. 3 resents the disposition of subjects in Part B.

Evaluations

Safety Evaluations

The safety and tolerability of ANTIBODY A including physical examinations, infusion reactions, injection site reactions, clinical laboratory tests, vital signs, concomitant medications, and treatment-emergent adverse events (TEAEs) were summarized by treatment groups. The safety and tolerability of ANTIBODY A including physical examinations, infusion reactions, injection site.

Pharmacokinetic and Immunogenicity

For all subjects participating in the study, serum samples were used to evaluate the PK, as well as the immunogenicity of ANTIBODY A. Serum samples were collected at specified times relative to the start of the infusion/injection as listed in FIG. 1.

Serum samples were analyzed to determine concentrations of ANTIBODY A using a validated, immunoassay method with a lower limit of quantification (LLOQ) of 0.06 µg/mL. The detection and characterization of antibodies to ANTIBODY A was performed using a validated assay method.

Pharmacodynamic Evaluation

Biopsy of skin lesions from subjects who provided (optional) biopsy consent, pre- and post-treatment biopsies of lesioned skin (2 pre- and 2 post-treatment; 4 mm punch) were taken. Biopsy specimens were to be assessed by mRNA expression and specific immunohistochemistry staining subject to adequacy of the specimen.

Clinical Response Evaluations

Response evaluations and patient reported quality of life measures were to include SLEDAI-2K/SLEDAI-2K Responder Index (S2K RI-50), British Isles Lupus Assessment Group (BILAG), Cutaneous Lupus Erythematosus Disease Area and Severity Index (CLASI), Physician's Global Assessment (PGA) of Disease Activity, Short-form—36 questionnaire, EuroQol—5 dimensions—5 levels (EQ-5D-5L) Patient Diary, Joint Assessment, and Photography of SLE subject skin lesions for subjects who provided consent to photography.

Glycoform Analysis

In Part A, subjects receiving 15 mg/kg had serum samples collected and stored. The samples could be analyzed in the future to determine the potential change in ANTIBODY A glycoform levels.

Biomarkers

Biomarkers were to be analyzed as part of the exploratory analyses for subjects in Parts A and B. This included serum levels of IFNs as well as molecular pathway profiling. These biomarkers included, but were not limited to, inflammatory markers, RNA, cell surface markers, autoantibodies, T-cell and B-cell repertoire, target-specific markers, and other categories of biomarkers potentially involved in the development and the progression of SLE.

Pharmacogenomic Evaluations

Samples were to be analyzed for the variability of RNA, DNA, protein expression, and changes in IFN signatures. Additional analyses were to be conducted if it was hypothesized that this can help resolve issues with the clinical data.

Statistical Methods

Clinical response analyses in Part B were to include summaries of SLE evaluations, including organ domain-specific changes.

Pharmacokinetics: Individual subject serum concentration-time data of ANTIBODY A were analyzed by non-compartmental analysis (NCA) and summarized by treatment group and planned sampling time point. PK parameters were summarized by treatment group and PK data were displayed graphically. Plots of the mean serum concentrations of ANTIBODY A over time were provided. Descriptive statistics were calculated for all individual derived PK parameters including exposure information of ANTIBODY A.

Immunogenicity: The status of antibodies to ANTIBODY A were summarized for all subjects who received a dose of ANTIBODY A and had appropriate samples for detection of antibodies to ANTIBODY A. Subjects with baseline positive samples and without increased titer post treatment were not considered anti-drug antibody (ADA) positive.

All TEAEs were summarized by treatment group and MedDRA versions 18.1 (Part A) and 21.0 (Part B), SOC and PTs for each group of healthy and SLE subjects.

Safety Results

The safety analysis sets included 48 subjects in Part A and 26 subjects in Part B. Overall, 39 (81.3%) subjects in Part A and 20 (76.9%) subjects in Part B reported ≥1 TEAEs during the course of study. The most common TEAE was reported in the system organ class of Infections and infestations for both the parts of the study.

In Part A, 1 subject treated with ANTIBODY A 0.3 mg/kg IV experienced a non-serious TEAE of myringitis bullosa of the right ear. The event was reported as resolved. No infusion reactions were reported and no local injection site reactivity was attributed to the study agent. No Serious TAEs were reported in Part A.

In Part B, serious TEAEs were reported by 2 (7.7%) subjects from the ANTIBODY A cohort: herpes zoster (HZ) by 2 (7.7%) subjects and premature labor by 1 (3.8%) subject. There were no serious TEAEs reported in the placebo cohort. One subject treated with ANTIBODY A 10.0 mg/kg IV discontinued the study due to a non-serious TEAE of groin pain (lymphadenopathy) which was considered to be possibly related to ANTIBODY A. No infusion reactions were reported and no local injection site reactivity was attributed to the study agents. Additionally, no TEAEs related to malignancy and no anaphylactic or serum sickness-type reactions were reported.

Overall, ANTIBODY A was well-tolerated by the normal healthy volunteers and SLE subjects. There were no deaths reported in the study.

In addition, no clinically significant changes from baseline were observed for laboratory parameters, vital signs, physical exam, or ECG findings.

Pharmacokinetics Results

Part A

Separate cohorts of healthy subjects received single ascending IV doses over a dose range of 0.3 to 15 mg/kg ANTIBODY A or placebo. In addition, one cohort of healthy subjects received a single SC dose of 1 mg/kg ANTIBODY A or placebo.

Figure 4:
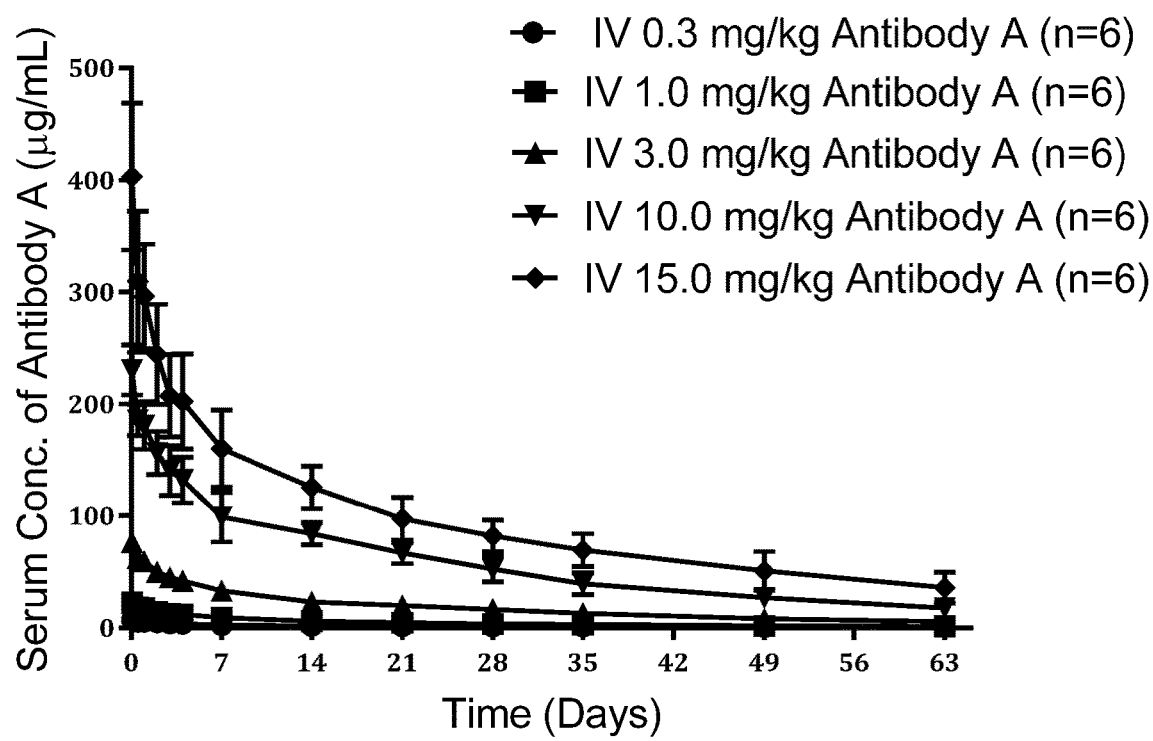
FIG. 4 demonstrates mean (SD) serum concentration-time profiles of ANTIBODY A after single intravenous infusion of ANTIBODY A at doses ranging from 0.3 to 15 mg/kg in healthy subjects (Cohorts 1-5).
Figure 5:
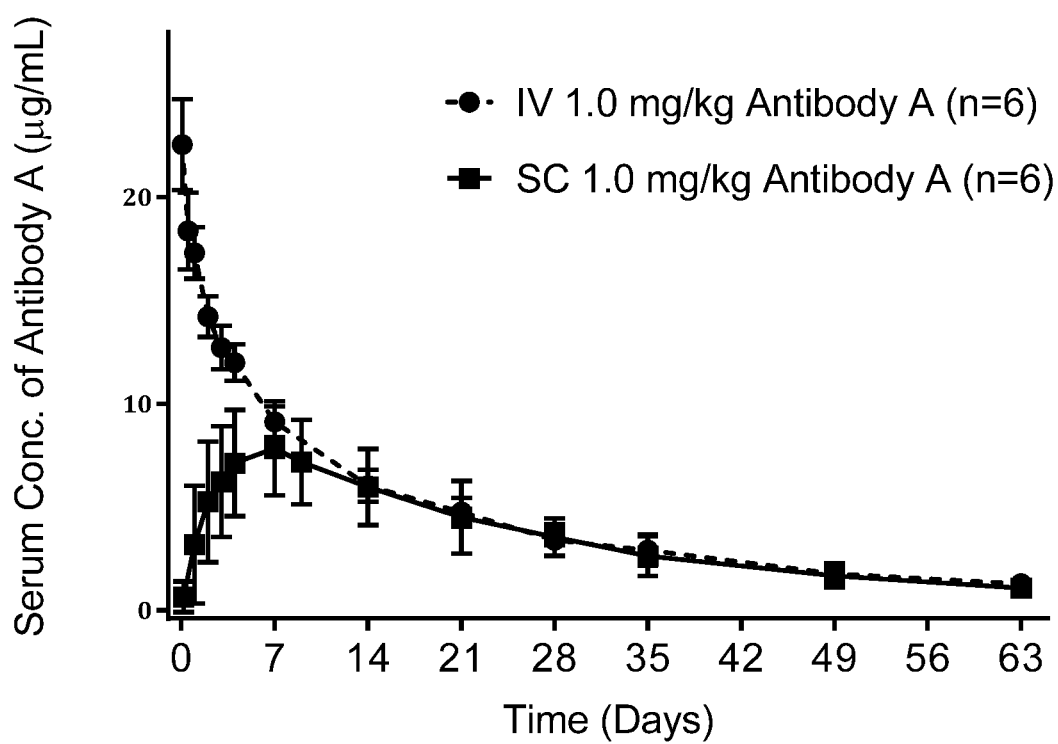
FIG. 5 demonstrates mean (SD) serum concentration-time profiles of ANTIBODY A after a single intravenous infusion of ANTIBODY A 1.0 mg/kg (Cohort 2) or after a single subcutaneous injection of ANTIBODY A 1.0 mg/kg (Cohort 6) in healthy subjects.

The linear mean serum concentration-time profiles of ANTIBODY A of Cohorts 1 to 5 (IV infusion) are presented in FIG. 4. The linear mean serum concentration-time profile of ANTIBODY A of Cohort 2 (1.0 mg/kg, IV infusion) and Cohort 6 (1.0 mg/kg, SC injection) is presented in FIG. 5.

A summary list of key PK parameters of ANTIBODY A for Cohorts 1 to 5 is presented in Table 11 below. Overall, in Part A, the maximum observed serum concentration of ANTIBODY A ($C_{max}$) and area under the curve (AUC) demonstrated an approximately dose-dependent and dose-proportional increase in the dose range of 0.3 mg/kg to 15 mg/kg, after single IV infusion in healthy subjects. Mean total systemic clearance after IV administration (CL) and volume of distribution at terminal phase ($V_z$) after a single IV infusion ranged between 2.28 and 3.09 mL/day/kg and between 67.2 and 102 mL/kg, respectively.

TABLE 11

Pharmacokinetic Results of ANTIBODY A After a Single Intravenous Infusion of ANTIBODY A at Doses Ranging from 0.3 to 15 mg/kg in Healthy Subjects (Cohorts 1-5)

| Pharmacokinetics of | Single IV infusion of ANTIBODY A | | | | |
|---|---|---|---|---|---|
| ANTIBODY A (mean [SD]) | 0.3 mg/kg (Cohort 1) | 1.0 mg/kg (Cohort 2) | 3.0 mg/kg (Cohort 3) | 10 mg/kg (Cohort 4) | 15 mg/kg (Cohort 5) |
| n | $6^a$ | 6 | $6^b$ | $6^b$ | $6^c$ |
| $C_{max}$ (µg/mL) | 7.14 (0.961) | 22.5 (2.21) | 76.5 (9.30) | 230 (22.4) | 403 (65.7) |
| $AUC_{0-t}$ (µg · day/mL) | 88.8 (12.6) | 287 (31.9) | 1143 (245) | 3694 (610) | 5944 (1036) |
| $AUC_{0-inf}$ (µg · day/mL) | 105 (18.6) | 331 (54.7) | 1225 (334) | 3999 (621) | 6780 (1259) |
| $T_{1/2}$ (day) | 24.6 (3.8) | 22.4 (5.1) | 20.7 (6.4) | 22.9 (4.3) | 24.1 (2.4) |
| CL (mL/day/kg) | 2.95 (0.675) | 3.09 (0.519) | 2.59 (0.645) | 2.55 (0.398) | 2.28 (0.446) |
| $V_Z$ (mL/kg) | 102 (4.54) | 97.2 (13.1) | 67.2 (7.98) | 78.8 (9.04) | 78.1 (8.57) |
| $C_{max,\ dose\ normalized}$ (µg/mL) | 23.8 (3.20) | 22.5 (2.21) | 25.5 (3.10) | 23.0 (2.24) | 26.9 (4.38) |
| $AUC_{0-t,\ dose\ normalized}$ (µg · day/mL) | 296 (41.9) | 287 (31.9) | 381 (81.6) | 369 (61.0) | 396 (69.1) |
| $AUC_{0-inf,\ dose\ normalized}$ (µg · day/mL) | 350 (61.9) | 331 (54.7) | 408 (111) | 400 (62.1) | 452 (83.9) |

$^a$n = 5 for $AUC_{0-t}$, $AUC_{0-inf}$, CL, $V_Z$, $AUC_{0-t}$, dose normalized, and $AUC_{0-inf}$ dose normalized
$^b$n = 5 for $AUC_{0-inf}$, CL, $V_Z$, and $AUC_{0-inf}$ dose normalized
$^c$n = 5 for $AUC_{0-inf}$, $T_{1/2}$, CL, $V_Z$, and $AUC_{0-inf}$ dose normalized A summary list of key PK parameters of ANTIBODY A for Cohorts 2 and 6 is presented in Table 2 below. After a single SC injection, mean $C_{max}$ (7.96 µg/mL) was reached after 7 days ($T_{max}$). Mean total systemic clearance after IV administration/(CL/F) and $V_z$/F were 3.96 mL/day/kg and 119 mL/kg, respectively. Terminal half-life (T1/2) was similar after IV infusion and SC injection. Mean T1/2 after a single IV infusion ranged from 20.7 to 24.6 days, and mean T1/2 after a SC injection was 22.6 days. The bioavailability of ANTIBODY A administered as a SC injection, based on the comparison with an IV infusion at the same dose, averaged 78.7% and 81.9% for FAUC0-t and FAUC0-inf, respectively.

TABLE 2

Pharmacokinetic Results of ANTIBODY A After a Single Intravenous Infusion of ANTIBODY A 1.0 mg/kg (Cohort 2) or After a Single Subcutaneous Injection of ANTIBODY A 1.0 mg/kg (Cohort 6) in Healthy Subjects

| Pharmacokinetics of ANTIBODY A (mean [SD], $T_{max}$: median [range]) | 1.0 mg/kg IV infusion of ANTIBODY A (Cohort 2) | 1.0 mg/kg SC injection of ANTIBODY A (Cohort 6) |
|---|---|---|
| n | 6 | $5^a$ |
| $C_{max}$ (µg/mL) | 22.5 (2.21) | 7.96 (2.48) |
| $T_{max}$ (day) | — | 6.96 (2.00-7.00) |
| $AUC_{0-t}$ (µg · day/mL) | 287 (31.9) | 226 (69.5) |
| $AUC_{0-inf}$ (µg · day/mL) | 331 (54.7) | 271 (87.3) |
| $T_{1/2}$ (day) | 22.4 (5.1) | 22.6 (4.1) |
| CL(/F) (mL/day/kg) | 3.09 (0.519) | 3.96 (1.14) |
| $V_z$(/F) (mL/kg) | 97.2 (13.1) | 119 (37.0) |

TABLE 2-continued

Pharmacokinetic Results of ANTIBODY A After a Single Intravenous Infusion of
ANTIBODY A 1.0 mg/kg (Cohort 2) or After a Single Subcutaneous Injection of
ANTIBODY A 1.0 mg/kg (Cohort 6) in Healthy Subjects

| Pharmacokinetics of ANTIBODY A (mean [SD], $T_{max}$: median [range]) | 1.0 mg/kg IV infusion of ANTIBODY A (Cohort 2) | 1.0 mg/kg SC injection of ANTIBODY A (Cohort 6) |
|---|---|---|
| $F_{AUC0-t}$ (%) | — | 78.7 (24.2) |
| $F_{AUC0-inf}$ (%) | — | 81.9 (26.4) |

$^a$n = 4 for $AUC_{0-inf}$, CL/F, $V_z$/F, and $F_{AUC0-inf}$

Part B

Figure 6:
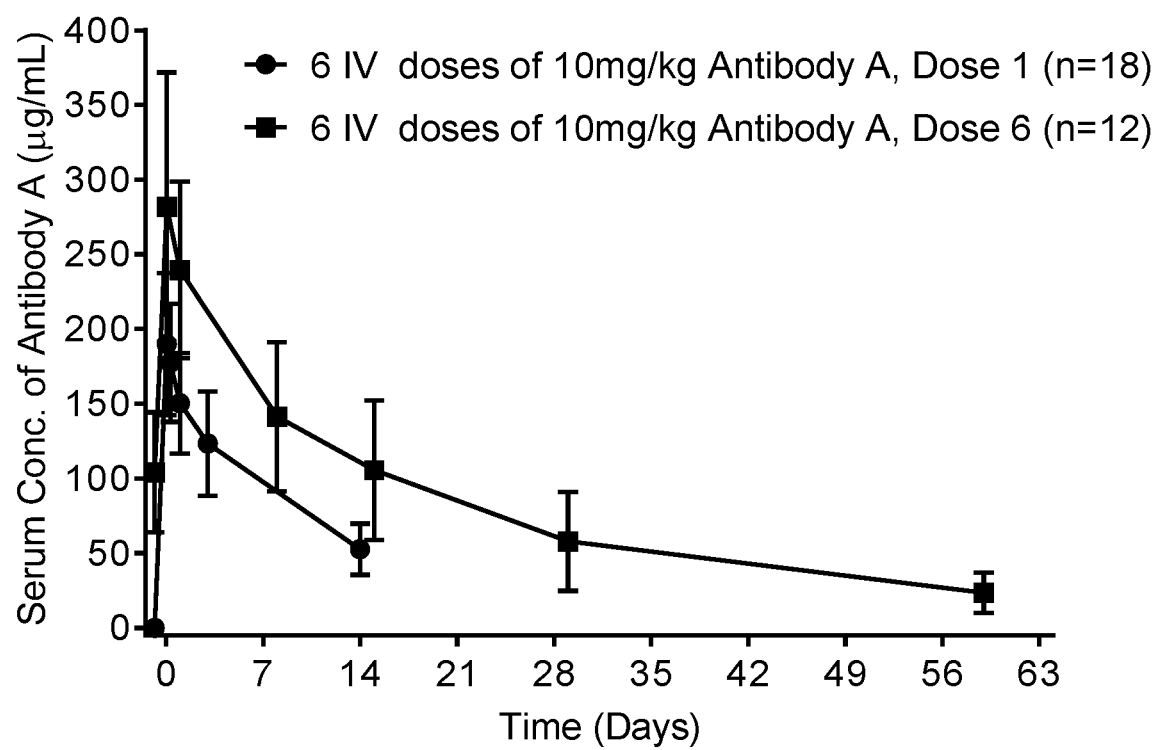
FIG. 6 demonstrates mean (SD) serum concentration-time profiles of ANTIBODY A after multiple intravenous infusions of 10 mg/kg ANTIBODY A in subjects with mild to moderate systemic lupus erythematosus.

In Part B of this study, 28 subjects with mild to moderate SLE were randomized to receive 6 doses of 10 mg/kg ANTIBODY A or placebo administered every 2 weeks as an IV infusion of at least 30 minutes. The linear mean serum concentration-time profiles of ANTIBODY A of Dose 1 and Dose 6 are presented in FIG. 6.

Following 6 doses of IV infusions of ANTIBODY A at 10 mg/kg every 2 weeks, the shape of the PK profiles of Dose 1 and Dose 6 were generally comparable up till 14 days postdose, i.e., 1 dosing interval. The PK profiles after Dose 1 and Dose 6 were similar to the PK profiles observed in healthy volunteers, with a bi-phasic disposition. Peak serum concentrations were approximately 1.5 times higher after Dose 6 compared to Dose 1. The exposure of ANTIBODY A during a dosing interval (areas under the curve for 0 to 14 days [AUC0-14d]) was higher after Dose 6 as compared to Dose 1.

A summary list of key PK parameters of ANTIBODY A is presented in Table 3 below. Based on the pre-dose plasma concentration ($C_{predose}$) concentrations of Dose 4, 5, and 6, steady-state conditions of ANTIBODY A appeared to be achieved within 43 days of treatment (Dose 4) with ANTIBODY A. Mean accumulation based on AUC was 1.86-fold. Mean accumulation based on $C_{max}$ was 1.62-fold after Dose 6 as compared to Dose 1. Mean values for CL and volume of distribution ($V_{ss}$) after the sixth dose were 4.73 mL/day/kg and 92.6 mL/kg, respectively. Mean T1/2 after the 6th dose was 14.8 days.

Although no formal comparison has been performed, the exposure in subjects with mild to moderate SLE seems slightly lower when compared to healthy subjects at an IV dose of 10 mg/kg.

TABLE 3

Pharmacokinetic Results of ANTIBODY A After Multiple
Intravenous Infusions of 10 mg/kg ANTIBODY A in Subjects
with Mild to Moderate Systemic Lupus Erythematosus

| Pharmacokinetics of ANTIBODY A (mean [SD]) | 10 mg/kg IV infusion of ANTIBODY A |
|---|---|
| Dose 1 | |
| n | 18$^a$ |
| $C_{max}$ (μg/mL) | 194 (46.3) |
| $AUC_{0-14d}$ (μg · day/mL) | 1387 (354) |
| Dose 4 | |
| n | 17 |
| $C_{predose}$ (μg/mL) | 107 (59.9) |
| Dose 5 | |
| n | 16 |
| $C_{predose}$ (μg/mL) | 101 (38.9) |
| Dose 6 | |
| n | 16$^b$ |
| $C_{predose}$ (μg/mL) | 104 (40.2) |
| $C_{max}$ (μg/mL) | 289 (72.6) |
| $AUC_{0-14d}$ (μg · day/mL) | 2340 (690) |
| $T_{1/2}$ (day) | 14.8 (4.4) |
| CL (mL/day/kg) | 4.73 (1.78) |
| $V_{ss}$ (mL/kg) | 92.6 (23.9) |
| $AR_{CMAX}$ (%) | 162.34 (74.50) |
| $AR_{AUC}$ (%) | 186.12 (115.15) |

$^a$n = 17 for $AUC_{0-14d}$
$^b$n = 17 for $C_{predose}$

Immunogenicity Results (Part A and Part B)

No subject developed antibody to ANTIBODY A following single administration of ANTIBODY A IV between 0.3 to 15 mg/kg or SC at 1 mg/kg in healthy subjects or multiple administrations of ANTIBODY A IV at 10 mg/kg in subjects with mild to moderate SLE. Therefore, no ADA incidence was calculated and reported.

Clinical Response Results from Part B

SLE Responder Index (SRI)-4, 5, and 6

The number of subjects with SRI-4, SRI-5 or SRI-6 response at day 100 is presented in Table 4. Data from the overall SRI response at day 100 indicates that subjects from the ANTIBODY A treatment group demonstrated numerically greater response rate than those in the placebo cohort (31.3% versus 0%, respectively).

TABLE 4

Number of Subjects with SRI-4, SRI-5 or
SRI-6 Response at day 100 in Part B; Full Analysis Set

| | Placebo | ANTIBODY A 10 mg/kg IV |
|---|---|---|
| Analysis Set: Full Analysis Set | 8 | 18 |
| Subjects evaluable for SRI response at day 100 | 8 | 16 |
| Number of subjects with SRI-4 response (%) | 0 | 5 (31.3%) |
| Number of subjects with SRI-5 response (%) | 0 | 2 (12.5%) |
| Number of subjects with SRI-6 response (%) | 0 | 2 (12.5%) |

Note:
SRI-4 response defined as ≥4 point reduction in SLEDAI-2K Total score, no new domain scores in either BILAG A or BILAG B and no worsening (<1 cm increase) from baseline in the Physician's Global Assessment of Disease Activity (PGA). SRI-5 and SRI-6 are defined similarly however a 5-point or 6-point reduction in SLEDAI-2K, respectively, is required.

BILAG

No new BILAG A or 2B shifts were noted, as shown in Table 5 below.

TABLE 5

Summary of Time to First SLEDAI, Severe SLEDAI or BILAG Flare from day 1 through day 100 in Part B

|  | Placebo | ANTIBODY A 10 mg/kg IV |
|---|---|---|
| Analysis Set: Full Analysis Set | 8 | 18 |
| Subjects with SLEDAI Flare from day 1 to day 100 | 1 (12.5%) | 3 (16.7%) |
| Time to First SLEDAI Flare |  |  |
| Mean (SD) | 18.0 (−) | 25.0 (8.66) |
| Median | 18.0 | 30.0 |
| Range | (18; 18) | (15; 30) |
| Subjects with Severe SLEDAI Flare from day 1 to day 100 | 0 | 0 |
| Time to First Severe SLEDAI Flare |  |  |
| Mean (SD) | — | — |
| Median | — | — |
| Range | — | — |
| Subjects with BILAG Flare from day 1 to day 100 | 0 | 0 |
| Time to First BILAG Flare |  |  |
| Mean (SD) | — | — |
| Median | — | — |
| Range | — | — |
| Subjects with SLEDAI, Severe SLEDAI or BILAG Flare from day 1 to day 100 | 1 (12.5%) | 3 (16.7%) |
| Time to First SLEDAI, Severe SLEDAI or BILAG Flare |  |  |
| Mean (SD) | 18.0 (−) | 25.0 (8.66) |
| Median | 18.0 | 30.0 |
| Range | (18; 18) | (15; 30) |

Note:
SLEDAI flare defined as ≥4 point increase in SLEDAI-2K score. Severe SLEDAI flare defined as ≥7 point increase in SLEDAI-2K score. BILAG flare defined as at least 1 new BILAG A or 2 new BILAG B scores (from scores < B). Time to flare defined as the time (in days) post baseline when the first flare occurs.

SLEDAI-2K

A summary of change and percent change from baseline in SLEDAI-2K over time are presented in Table 6. Overall, data from the ANTIBODY A cohort demonstrated numerically greater reduction that that from the placebo cohort: mean (SD) percentage change from baseline at day 100 for SLEDAI-2K: −23.74 (27.061) versus −8.93 (13.139), respectively.

TABLE 6

Summary of Change and Percent Change from Baseline in SLEDAI-2K over Time in Part B

|  | Placebo | ANTIBODY A 10 mg/kg IV |
|---|---|---|
| Analysis Set: Full Analysis Set SLEDAI-2K (0-105) | 8 | 18 |
| Baseline Mean (SD) | 9.5 (3.16) | 8.9 (3.64) |
| Baseline Median | 10.0 | 8.5 |
| Subjects evaluable at day 15 | 6 | 15 |
| Baseline Mean (SD) | 9.7 (1.97) | 9.1 (3.91) |
| Baseline Median | 10.0 | 9.0 |

TABLE 6-continued

Summary of Change and Percent Change from Baseline in SLEDAI-2K over Time in Part B

|  | Placebo | ANTIBODY A 10 mg/kg IV |
|---|---|---|
| Change from baseline |  |  |
| Mean (SD) | −0.3 (3.88) | −0.7 (2.97) |
| Median | 0.0 | 0.0 |
| Range | (−6; 6) | (−8; 6) |
| IQ range | (−2.0; 0.0) | (−2.0; 0.0) |
| Percent change from baseline |  |  |
| Mean (SD) | 5.00 (50.498) | −1.71 (30.468) |
| Median | 0.00 | 0.00 |
| Range | (−50.0; 100.0) | (−40.0; 75.0) |
| IQ range | (−20.00; 0.00) | (−25.00; 0.00) |
| Subjects evaluable at Day 29 | 7 | 16 |
| Baseline Mean (SD) | 10.3 (2.43) | 9.2 (3.78) |
| Baseline Median | 10.0 | 9.5 |
| Change from baseline |  |  |
| Mean (SD) | −1.3 (2.63) | 0.1 (3.54) |
| Median | 0.0 | 0.0 |
| Range | (−6; 2) | (−8; 6) |
| IQ range | (−3.0; 0.0) | (−2.0; 2.0) |
| Percent change from baseline |  |  |
| Mean (SD) | −8.30 (25.770) | 8.13 (37.991) |
| Median | 0.00 | 0.00 |
| Range | (−50.0; 33.3) | (−50.0; 75.0) |
| IQ range | (−21.40; 0.00) | (−16.70; 35.00) |
| Subjects evaluable at Day 57 | 6 | 16 |
| Baseline Mean (SD) | 9.7 (1.97) | 9.2 (3.78) |
| Baseline Median | 10.0 | 9.5 |
| Change from baseline |  |  |
| Mean (SD) | 0.7 (3.27) | −1.9 (2.74) |
| Median | 0.0 | −1.0 |
| Range | (−4; 6) | (−8; 2) |
| IQ range | (0.0; 2.0) | (−4.0; 0.0) |
| Percent change from baseline |  |  |
| Mean (SD) | 14.45 (45.290) | −16.39 (29.462) |
| Median | 0.00 | −8.35 |
| Range | (−33.3; 100.0) | (−75.0; 50.0) |
| IQ range | (0.00; 20.00) | (−40.00; 0.00) |
| Subjects evaluable at Day 71 | 8 | 16 |
| Baseline Mean (SD) | 9.5 (3.16) | 9.2 (3.78) |
| Baseline Median | 10.0 | 9.5 |
| Change from baseline |  |  |
| Mean (SD) | −1.0 (2.98) | −2.8 (4.06) |
| Median | −0.5 | −2.0 |
| Range | (−6; 3) | (−16; 0) |
| IQ range | (−3.0; 1.0) | (−3.0; 0.0) |
| Percent change from baseline |  |  |
| Mean (SD) | −4.83 (30.547) | −25.76 (27.567) |
| Median | −5.00 | −19.45 |
| Range | (−50.0; 50.0) | (−80.0; 0.0) |
| IQ range | (−24.30; 10.00) | (−41.65; 0.00) |
| Subjects evaluable at day 100 | 8 | 16 |
| Baseline Mean (SD) | 9.5 (3.16) | 9.0 (3.86) |
| Baseline Median | 10.0 | 9.0 |
| Change from baseline |  |  |
| Mean (SD) | −0.9 (1.25) | −2.1 (2.68) |
| Median | 0.0 | −2.0 |
| Range | (−3; 0) | (−8; 2) |
| IQ range | (−2.0; 0.0) | (−4.0; 0.0) |
| Percent change from baseline |  |  |
| Mean (SD) | −8.93 (13.139) | −23.74 (27.061) |
| Median | 0.00 | −22.50 |
| Range | (−33.3; 0.0) | (−75.0; 20.0) |
| IQ range | (−19.05; 0.00) | (−36.65; 0.00) |

S2K RI-50

A summary of change and percent change from baseline in S2K RI-50 over time are presented in Table 7. Overall, data from the ANTIBODY A cohort demonstrated numerically greater reduction that that from the placebo cohort: mean (SD) percentage change from baseline at day 100 for S2K RI-50: −51.77 (24.760) versus −25.84 (22.163), respectively.

TABLE 7

Summary of Change and Percent Change from Baseline in S2K RI-50 Over Time in Part B

|  | Placebo | ANTIBODY A 10 mg/kg IV |
|---|---|---|
| Analysis Set: Full Analysis Set SLEDAI-2K RI-50 (0-105) | 8 | 18 |
| Baseline Mean (SD) | 9.3 (3.69) | 8.8 (3.70) |
| Baseline Median | 10.0 | 8.5 |
| Subjects evaluable at day 15 | 8 | 17 |
| Baseline Mean (SD) | 9.3 (3.69) | 9.0 (3.74) |
| Baseline Median | 10.0 | 9.0 |
| Change from baseline |  |  |
| Mean (SD) | −1.8 (4.20) | −3.2 (4.34) |
| Median | −2.0 | −3.0 |
| Range | (−6; 4) | (−14; 6) |
| IQ range | (−6.0; 2.0) | (−4.0; 0.0) |
| Percent change from baseline |  |  |
| Mean (SD) | 9.23 (86.610) | −29.71 (36.825) |
| Median | −20.00 | −33.30 |
| Range | (−60.0; 200.0) | (−70.0; 75.0) |
| IQ range | (−46.45; 33.35) | (−60.00; 0.00) |
| Subjects evaluable at Day 29 | 8 | 17 |
| Baseline Mean (SD) | 9.3 (3.69) | 9.0 (3.74) |
| Baseline Median | 10.0 | 9.0 |
| Change from baseline |  |  |
| Mean (SD) | −3.1 (2.36) | −3.6 (5.00) |
| Median | −2.0 | −2.0 |
| Range | (−7; 0) | (−16; 4) |
| IQ range | (−5.0; −2.0) | (−6.0; 0.0) |
| Percent change from baseline |  |  |
| Mean (SD) | −29.16 (17.342) | −30.52 (40.095) |
| Median | −26.65 | −25.00 |
| Range | (−50.0; 0.0) | (−83.3; 50.0) |
| IQ range | (−45.00; −20.00) | (−66.70; 0.00) |
| Subjects evaluable at Day 57 | 8 | 17 |
| Baseline Mean (SD) | 9.3 (3.69) | 9.0 (3.74) |
| Baseline Median | 10.0 | 9.0 |
| Change from baseline |  |  |
| Mean (SD) | −2.8 (4.27) | −5.1 (4.68) |
| Median | −2.0 | −6.0 |
| Range | (−8; 4) | (−18; 0) |
| IQ range | (−7.0; 0.0) | (−8.0; −2.0) |
| Percent change from baseline |  |  |
| Mean (SD) | −19.64 (43.872) | −47.25 (35.444) |
| Median | −20.00 | −50.00 |
| Range | (−66.7; 66.7) | (−100.0; 0.0) |
| IQ range | (−58.55; 0.00) | (−75.00; −20.00) |
| Subjects evaluable at Day 71 | 8 | 17 |
| Baseline Mean (SD) | 9.3 (3.69) | 9.0 (3.74) |
| Baseline Median | 10.0 | 9.0 |
| Change from baseline |  |  |
| Mean (SD) | −2.0 (3.66) | −5.9 (4.68) |
| Median | −2.5 | −6.0 |
| Range | (−6; 5) | (−20; 0) |
| IQ range | (−5.0; 0.0) | (−8.0; −2.0) |

TABLE 7-continued

Summary of Change and Percent Change from Baseline in S2K RI-50 Over Time in Part B

|  | Placebo | ANTIBODY A 10 mg/kg IV |
|---|---|---|
| Percent change from baseline |  |  |
| Mean (SD) | −12.45 (42.994) | −58.45 (28.625) |
| Median | −25.00 | −60.00 |
| Range | (−50.0; 83.3) | (−100.0; 0.0) |
| IQ range | (−41.45; 0.00) | (−77.80; −33.30) |
| Subjects evaluable at day 100 | 8 | 18 |
| Baseline Mean (SD) | 9.3 (3.69) | 8.8 (3.70) |
| Baseline Median | 10.0 | 8.5 |
| Change from baseline |  |  |
| Mean (SD) | −2.9 (2.59) | −4.9 (3.52) |
| Median | −2.0 | −4.0 |
| Range | (−7; 0) | (−14; 0) |
| IQ range | (−5.0; −1.0) | (−7.0; −2.0) |
| Percent change from baseline |  |  |
| Mean (SD) | −25.84 (22.163) | −51.77 (24.760) |
| Median | −20.00 | −50.00 |
| Range | (−60.0; 0.0) | (−100.0; 0.0) |
| IQ range | (−45.00; −8.35) | (−70.00; −33.30) |

PGA

A summary of change and percent change from baseline in PGA is presented in Table 8. Overall, data from the ANTIBODY A cohort demonstrated numerically greater reduction of PGA than that from the placebo cohort (mean [SD] percentage change from baseline at day 100: −19.60 (36.250) versus −6.09 (29.154), respectively).

TABLE 8

Summary of Change and Percent Change from Baseline in PGA in Part B

|  | Placebo | ANTIBODY A 10 mg/kg IV |
|---|---|---|
| Analysis Set: Full Analysis Set Physician's Global Assessment (PGA VAS 0-10) | 8 | 18 |
| Baseline Mean (SD) | 3.00 (1.410) | 2.74 (1.300) |
| Baseline Median | 2.50 | 2.40 |
| Subjects evaluable at day 15 | 8 | 17 |
| Baseline Mean (SD) | 3.00 (1.410) | 2.68 (1.313) |
| Baseline Median | 2.50 | 2.30 |
| Change from baseline |  |  |
| Mean (SD) | −0.44 (0.933) | 0.02 (0.623) |
| Median | −0.35 | 0.00 |
| Range | (−2.0; 1.0) | (−1.0; 1.5) |
| IQ range | (−0.95; 0.05) | (−0.40; 0.20) |
| Percent change from baseline |  |  |
| Mean (SD) | −1.73 (44.697) | 4.48 (30.382) |
| Median | −11.01 | 0.00 |
| Range | (−50.0; 100.0) | (−33.3; 71.4) |
| IQ range | (−22.73; 1.83) | (−14.29; 14.29) |
| Subjects evaluable at Day 29 | 8 | 17 |
| Baseline Mean (SD) | 3.00 (1.410) | 2.68 (1.313) |
| Baseline Median | 2.50 | 2.30 |
| Change from baseline |  |  |
| Mean (SD) | −0.39 (1.236) | 0.15 (1.232) |
| Median | 0.05 | −0.10 |
| Range | (−3.1; 0.8) | (−1.0; 4.3) |
| IQ range | (−0.75; 0.30) | (−0.40; 0.50) |

TABLE 8-continued

Summary of Change and Percent Change from Baseline in PGA in Part B

|  | Placebo | ANTIBODY A 10 mg/kg IV |
|---|---|---|
| Percent change from baseline | | |
| Mean (SD) | −3.34 (46.204) | 12.42 (67.063) |
| Median | 0.91 | −4.76 |
| Range | (−77.5; 80.0) | (−43.5; 252.9) |
| IQ range | (−27.92; 12.38) | (−17.39; 16.67) |
| Subjects evaluable at Day 57 | 8 | 17 |
| Baseline Mean (SD) | 3.00 (1.410) | 2.68 (1.313) |
| Baseline Median | 2.50 | 2.30 |
| Change from baseline | | |
| Mean (SD) | −0.60 (1.664) | −0.61 (0.797) |
| Median | −0.80 | −0.50 |
| Range | (−3.9; 1.5) | (−2.2; 1.3) |
| IQ range | (−1.00; 0.60) | (−1.00; −0.10) |
| Percent change from baseline | | |
| Mean (SD) | −3.86 (66.434) | −18.72 (28.865) |
| Median | −21.59 | −22.73 |
| Range | (−97.5; 120.0) | (−48.3; 76.5) |
| IQ range | (−35.12; 30.00) | (−34.92; −9.52) |
| Subjects evaluable at Day 71 | 8 | 17 |
| Baseline Mean (SD) | 3.00 (1.410) | 2.68 (1.313) |
| Baseline Median | 2.50 | 2.30 |
| Change from baseline | | |
| Mean (SD) | −0.03 (1.430) | −0.42 (1.213) |
| Median | −0.50 | −0.60 |
| Range | (−1.5; 3.0) | (−2.1; 2.3) |
| IQ range | (−0.95; 0.60) | (−1.10; 0.10) |
| Percent change from baseline | | |
| Mean (SD) | 3.60 (46.142) | −3.77 (57.836) |
| Median | −18.61 | −26.09 |
| Range | (−37.5; 75.0) | (−62.5; 135.3) |
| IQ range | (−30.75; 45.00) | (−34.78; 2.86) |
| Subjects evaluable at day 100 | 8 | 18 |
| Baseline Mean (SD) | 3.00 (1.410) | 2.74 (1.300) |
| Baseline Median | 2.50 | 2.40 |
| Change from baseline | | |
| Mean (SD) | −0.40 (0.959) | −0.71 (1.060) |
| Median | −0.40 | −0.55 |
| Range | (−2.0; 1.0) | (−3.3; 1.5) |
| IQ range | (−1.00; 0.30) | (−1.00; −0.10) |
| Percent change from baseline | | |
| Mean (SD) | −6.09 (29.154) | −19.60 (36.250) |
| Median | −15.89 | −30.95 |
| Range | (−50.0; 40.0) | (−57.1; 100.0) |
| IQ range | (−21.82; 18.33) | (−39.13; −14.29) |

Joint Assessment:

A summary of change from baseline in the number of joints with pain and signs of inflammation over time for subjects with at least 2 affected joints at baseline is presented in Table 9.

TABLE 9

Summary of Change from Baseline in Number of Joints with Pain and Signs of Inflammation Over Time for Subjects with at Least 2 Affected Joints at Baseline in Part B

|  | Placebo | ANTIBODY A 10 mg/kg IV |
|---|---|---|
| Analysis Set: Full Analysis Set | 8 | 18 |
| Subjects with at Least 2 Joints with Pain and Signs of Inflammation (Tenderness, Swelling or Effusion) at Baseline | 4 | 6 |
| Baseline Mean (SD) | 4.5 (3.00) | 2.3 (0.52) |
| Baseline Median | 3.0 | 2.0 |
| Change from Baseline in Number of Joints with Pain and Signs of Inflammation (Tenderness, Swelling or Effusion) | | |
| Subjects evaluable at day 15 | 4 | 6 |
| Baseline Mean (SD) | 4.5 (3.00) | 2.3 (0.52) |
| Baseline Median | 3.0 | 2.0 |
| Change from baseline | | |
| Mean (SD) | −2.0 (1.41) | −1.0 (1.55) |
| Median | −2.5 | −1.5 |
| Range | (−3; 0) | (−2; 2) |
| IQ range | (−3.0; −1.0) | (−2.0; −1.0) |
| Subjects evaluable at Day 29 | 4 | 6 |
| Baseline Mean (SD) | 4.5 (3.00) | 2.3 (0.52) |
| Baseline Median | 3.0 | 2.0 |
| Change from baseline | | |
| Mean (SD) | 2.5 (7.05) | −1.7 (0.82) |
| Median | −0.5 | −2.0 |
| Range | (−2; 13) | (−2; 0) |
| IQ range | (−1.5; 6.5) | (−2.0; −2.0) |
| Subjects evaluable at Day 57 | 4 | 6 |
| Baseline Mean (SD) | 4.5 (3.00) | 2.3 (0.52) |
| Baseline Median | 3.0 | 2.0 |

TABLE 9-continued

Summary of Change from Baseline in Number of Joints
with Pain and Signs of Inflammation Over Time for Subjects
with at Least 2 Affected Joints at Baseline in Part B

|  | Placebo | ANTIBODY A 10 mg/kg IV |
|---|---|---|
| Change from baseline |  |  |
| Mean (SD) | −1.8 (0.50) | −1.2 (0.75) |
| Median | −2.0 | −1.0 |
| Range | (−2; −1) | (−2; 0) |
| IQ range | (−2.0; −1.5) | (−2.0; −1.0) |
| Subjects evaluable at day 71 | 4 | 6 |
| Baseline Mean (SD) | 4.5 (3.00) | 2.3 (0.52) |
| Baseline Median | 3.0 | 2.0 |
| Change from baseline |  |  |
| Mean (SD) | −1.3 (0.96) | −1.8 (0.41) |
| Median | −1.5 | −2.0 |
| Range | (−2; 0) | (−2; −1) |
| IQ range | (−2.0; −0.5) | (−2.0; −2.0) |
| Subjects evaluable at day 100 | 4 | 6 |
| Baseline Mean (SD) | 4.5 (3.00) | 2.3 (0.52) |
| Baseline Median | 3.0 | 2.0 |
| Change from baseline |  |  |
| Mean (SD) | −1.3 (1.71) | −1.2 (1.60) |
| Median | −1.5 | −2.0 |
| Range | (−3; 1) | (−2; 2) |
| IQ range | (−2.5; 0.0) | (−2.0; −1.0) |
| Subjects with at Least 2 Joints with Tenderness (pain) at Baseline | 4 | 6 |
| Change from Baseline in Number of Joints with Tenderness (pain) |  |  |
| Subjects evaluable at day 15 | 4 | 6 |
| Baseline Mean (SD) | 4.5 (3.00) | 2.3 (0.52) |
| Baseline Median | 3.0 | 2.0 |
| Range IQ range | (−8; 17) | (−11; 2) |
| Subjects evaluable at day 57 | (−5.5; 8.0) | (−3.0; −2.0) |
|  | 4 | 9 |
| Baseline Mean (SD) | 7.5 (4.36) | 9.9 (6.57) |
| Baseline Median | 6.5 | 9.0 |
| Change from baseline |  |  |
| Mean (SD) | −2.8 (4.50) | −4.4 (3.61) |
| Median | −1.5 | −3.0 |
| Range | (−9; 1) | (−10; 0) |
| IQ range | (−6.0; 0.5) | (−8.0; −2.0) |
| Subjects evaluable at day 71 | 4 | 9 |
| Baseline Mean (SD) | 7.5 (4.36) | 9.9 (6.57) |
| Baseline Median | 6.5 | 9.0 |
| Change from baseline |  |  |
| Mean (SD) | −1.8 (6.99) | −5.2 (6.91) |
| Median | −2.0 | −2.0 |
| Range | (−10; 7) | (−20; 2) |
| IQ range | (−6.5; 3.0) | (−5.0; −2.0) |
| Subjects evaluable at day 100 | 4 | 9 |
| Baseline Mean (SD) | 7.5 (4.36) | 9.9 (6.57) |
| Baseline Median | 6.5 | 9.0 |
| Change from baseline |  |  |
| Mean (SD) | −2.0 (2.45) | −4.9 (4.01) |
| Median | −1.5 | −4.0 |
| Range | (−5; 0) | (−12; 1) |
| IQ range | (−4.0; 0.0) | (−7.0; −2.0) |

A summary of change from baseline in the number of joints with pain and signs of inflammation over time is presented in Table 10.

TABLE 10

Summary of Change from Baseline in Number of
Joints with Pain and Signs of Inflammation Over Time in Part B

|  | Placebo | ANTIBODY A 10 mg/kg IV |
|---|---|---|
| Analysis Set: Full Analysis Set | 8 | 18 |
| Subjects evaluable for Joints with Pain and Signs of Inflammation (Tenderness, Swelling or Effusion) at Baseline | 8 | 18 |
| Baseline Mean (SD) | 2.8 (2.71) | 1.2 (0.94) |
| Baseline Median | 2.0 | 1.0 |
| Change from Baseline in Number of Joints with Pain and Signs of Inflammation (Tenderness, Swelling or Effusion) | | |
| Subjects evaluable at day 15 | 8 | 17 |
| Baseline Mean (SD) | 2.8 (2.71) | 1.2 (0.97) |
| Baseline Median | 2.0 | 1.0 |
| Change from baseline | | |
| Mean (SD) | −1.0 (1.41) | −0.4 (1.00) |
| Median | 0.0 | 0.0 |
| Range | (−3; 0) | (−2; 2) |
| IQ range | (−2.5; 0.0) | (−1.0; 0.0) |
| Subjects evaluable at day 29 | 8 | 17 |
| Baseline Mean (SD) | 2.8 (2.71) | 1.2 (0.97) |
| Baseline Median | 2.0 | 1.0 |
| Change from baseline | | |
| Mean (SD) | 1.3 (4.80) | −0.6 (0.93) |
| Median | 0.0 | 0.0 |
| Range | (−2; 13) | (−2; 0) |
| IQ range | (−0.5; 0.0) | (−2.0; 0.0) |
| Subjects evaluable at day 57 | 8 | 17 |
| Baseline Mean (SD) | 2.8 (2.71) | 1.2 (0.97) |
| Baseline Median | 2.0 | 1.0 |
| Change from baseline | | |
| Mean (SD) | −0.9 (0.99) | −0.4 (0.71) |
| Median | −0.5 | 0.0 |
| Range | (−2; 0) | (−2; 0) |
| IQ range | (−2.0; 0.0) | (−1.0; 0.0) |
| Subjects evaluable at day 71 | 8 | 17 |
| Baseline Mean (SD) | 2.8 (2.71) | 1.2 (0.97) |
| Baseline Median | 2.0 | 1.0 |
| Change from baseline | | |
| Mean (SD) | −0.6 (0.92) | −0.6 (1.00) |
| Median | 0.0 | 0.0 |
| Range | (−2; 0) | (−2; 1) |
| IQ range | (−1.5; 0.0) | (−2.0; 0.0) |
| Subjects evaluable at day 100 | 8 | 18 |
| Baseline Mean (SD) | 2.8 (2.71) | 1.2 (0.94) |
| Baseline Median | 2.0 | 1.0 |
| Change from baseline | | |
| Mean (SD) | −0.8 (1.28) | −0.3 (1.08) |
| Median | −0.5 | 0.0 |
| Range | (−3; 1) | (−2; 2) |
| IQ range | (−1.5; 0.0) | (−1.0; 0.0) |
| Subjects with Tenderness (pain) at Baseline | 8 | 18 |
| Change from Baseline in Number of Joints with Tenderness (pain) | | |
| Subjects evaluable at day 15 | 8 | 17 |
| Baseline Mean (SD) | 2.8 (2.71) | 1.2 (1.01) |
| Baseline Median | 2.0 | 1.0 |
| Change from baseline | | |
| Mean (SD) | −0.9 (1.36) | −0.4 (0.87) |
| Median | 0.0 | 0.0 |
| Range | (−3; 0) | (−2; 1) |
| IQ range | (−2.0; 0.0) | (−1.0; 0.0) |
| Subjects evaluable at day 29 | 8 | 17 |
| Baseline Mean (SD) | 2.8 (2.71) | 1.2 (1.01) |
| Baseline Median | 2.0 | 1.0 |

TABLE 10-continued

Summary of Change from Baseline in Number of
Joints with Pain and Signs of Inflammation Over Time in Part B

|  | Placebo | ANTIBODY A 10 mg/kg IV |
|---|---|---|
| Change from baseline | | |
| Mean (SD) | 1.8 (6.20) | −0.6 (0.94) |
| Median | 0.0 | 0.0 |
| Range | (−2; 17) | (−2; 0) |
| IQ range | (−0.5; 0.0) | (−2.0; 0.0) |
| Subjects evaluable at day 57 | 8 | 17 |
| Baseline Mean (SD) | 2.8 (2.71) | 1.2 (1.01) |
| Baseline Median | 2.0 | 1.0 |
| Change from baseline | | |
| Mean (SD) | −1.5 (2.07) | −0.4 (0.79) |
| Median | −1.0 | 0.0 |
| Range | (−6; 0) | (−2; 1) |
| IQ range | (−2.0; 0.0) | (−1.0; 0.0) |
| Subjects evaluable at day 71 | 8 | 17 |
| Baseline Mean (SD) | 2.8 (2.71) | 1.2 (1.01) |
| Baseline Median | 2.0 | 1.0 |
| Change from baseline | | |
| Mean (SD) | −0.9 (0.99) | 0.4 (3.92) |
| Median | −0.5 | 0.0 |
| Range | (−2; 0) | (−2; 15) |
| IQ range | (−2.0; 0.0) | (−2.0; 0.0) |
| Subjects evaluable at day 100 | 8 | 18 |
| Baseline Mean (SD) | 2.8 (2.71) | 1.2 (0.99) |
| Baseline Median | 2.0 | 1.0 |
| Change from baseline | | |
| Mean (SD) | −1.5 (2.56) | −0.3 (1.13) |
| Median | −0.5 | 0.0 |
| Range | (−7; 1) | (−2; 2) |
| IQ range | (−2.5; 0.0) | (−1.0; 0.0) |
| Subjects with Swelling or Effusion at Baseline | 8 | 18 |
| Change from Baseline in Number of Joints with Swelling or Effusion | | |
| Subjects evaluable at day 15 | 8 | 17 |
| Baseline Mean (SD) | 4.3 (4.50) | 5.6 (6.57) |
| Baseline Median | 2.5 | 3.0 |
| Change from baseline | | |
| Mean (SD) | −1.9 (3.83) | −0.6 (5.03) |
| Median | 0.0 | 0.0 |
| Range | (−11; 0) | (−16; 8) |
| IQ range | (−2.0; 0.0) | (−1.0; 2.0) |
| Subjects evaluable at day 29 | 8 | 17 |
| Baseline Mean (SD) | 4.3 (4.50) | 5.6 (6.57) |
| Baseline Median | 2.5 | 3.0 |
| Change from baseline | | |
| Mean (SD) | 0.6 (7.17) | −1.5 (2.96) |
| Median | 0.0 | 0.0 |
| Range | (−8; 17) | (−11; 2) |
| IQ range | (−2.0; 0.0) | (−2.0; 0.0) |

Overall, data from the ANTIBODY A cohort showed greater reduction in the number of swollen joints than that from the placebo cohort.

Flares

A summary of time to first SLEDAI, severe SLEDAI or BILAG flare from day 1 through day 100 is presented in Table 6 above. Due to the small number of total flares comparisons between the cohorts were difficult; however, there were no notable differences between the treatment groups.

CLASI

Low baseline activity scores rendered interpretation difficult. Judging by the percentage of subjects who experienced a 3-point deduction or 18% deduction from baseline at day 100 (defined as change in CLASI score that corresponds to clinical improvement), the ANTIBODY A cohort showed greater response than the placebo cohort (44.4% vs 25.0%, respectively).

EQ-5D-5L and SF-36

No changes were evident in the overall scores or individual domains across the cohorts.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present inventions as defined by the specific description.

We claim:

1. A method of treating Systemic Lupus Erythematosus (SLE) in a human subject in need thereof comprising subcutaneously or intravenously administering an anti-IFN-α/-ω antibody to the subject as a pharmaceutical composition comprising a formulation selected form the group consisting of:

a.) about 30 mg/mL of the anti-IFN-α/-ω antibody, about 5 mM lactate, about 5% (w/v) lactose, and about 0.02% (w/v) polysorbate 80 (PS80), at pH 5.5;

b.) about 40 mg/mL of the anti-IFN-α/-ω antibody, about 8 mM acetate, about 8% (w/v) maltose, and about 0.06% (w/v) polysorbate 20 (PS20), at pH 5.0;

c.) about 50 mg/mL of the anti-IFN-α/-ω antibody, about 13 mM acetate, about 8.0% (w/v) sucrose, and about 0.04% (w/v) polysorbate 20 (PS20), at pH 5.2;

d.) about 60 mg/mL of the anti-IFN-α/-ω antibody, about 10 mM acetate, about 8% (w/v) lactose, and about 0.06% (w/v) polysorbate 20 (PS20), at pH 5.4; and e.) about 70 mg/mL of the anti-IFN-α/-ω antibody, about 15 mM lactate, about 10% (w/v) maltose, and about 0.06% (w/v) polysorbate 80 (PS80), at pH 5.0;

wherein the antibody comprises a heavy chain variable region and a light chain variable region, the heavy chain variable region comprising heavy chain complementarity determining regions (HCDRs) HCDR1, HCDR2 and HCDR3 amino acid sequences of SEQ ID NOs: 33, 34, and 35, respectively, and the light chain variable region comprising light chain complementarity determining regions (LCDRs) LCDR1, LCDR2 and LCDR3 amino acid sequences of SEQ ID NOs: 30, 31, and 32, respectively, and wherein a total dosage of the antibody administered is about 0.1 mg/kg, about 0.3 mg/kg, about 1 mg/kg, about 3 mg/kg, about 10 mg/kg, about 15 mg/kg or about 20 mg/kg body weight of the subject per administration.

2. The method of claim 1, wherein the antibody comprises a heavy chain variable region (VH) having the amino acid sequence of SEQ ID NO: 28 and a light chain variable region (VL) having the amino acid sequences of SEQ ID NO: 29.

3. The method of claim 1, wherein the method achieves, in the plasma of the subject, at least one parameter selected from: (i) an area under the concentration time curve (AUC)$_{(0-t)}$ of about 50 μg·day/mL to about 7000 μg·day/mL, and (ii) a maximum concentration observed ($C_{max}$) of about 5 μg/mL to about 500 μg/mL.

4. The method of claim 1, wherein the administering of the anti-IFN-α/-ω antibody does not result in production of antibodies against the anti-IFN-α/-ω antibody in the subject.

5. The method of claim 1, wherein the human subject is in need of a treatment of mild to moderate systemic lupus erythematosus (SLE).

6. The method of claim 5, wherein the pharmaceutical composition is administered to the human subject intravenously for no less than 30 minutes in a total dosage of the anti-IFN-α/-ω antibody of about 10 mg/kg body weight of the subject per administration.

7. The method of claim 5, wherein the pharmaceutical composition is administered to the human subject subcutaneously in a total dosage of the anti-IFN-α/-ω antibody of about 1 mg/kg body weight of the subject per administration.

8. The method of claim 5, wherein the administering of the pharmaceutical composition achieves, in the plasma of the subject, at least one parameter selected from: (1) an area under the concentration time curve (AUC)$_{(0-14d)}$ of about 1000 μg·day/mL to about 3500 μg·day/mL, and (ii) a maximum concentration observed ($C_{max}$) of about 120 μg/mL to about 400 μg/mL.

9. The method of claim 5, wherein the human subject has a reduction in a Systemic Lupus Erythematosus Responder Index (SRI) of 4 points, 5 points, or 6 points, by day 100 after the administration of the pharmaceutical composition.

10. The method of claim 5, wherein the human subject has no new British Isles Lupus Assessment Group (BILAG) A or 2B shifts by day 100 after the administration of the pharmaceutical composition.

11. The method of claim 5, wherein the human subject has a reduction in a Systemic Lupus Erythematosus 2000 Responder Index-50 (S2K RI-50) from baseline by day 100 after the administration of the pharmaceutical composition.

12. The method of claim 5, wherein the human subject has a reduction in a Physician's Global Assessment of Disease Activity (PGA) from baseline by day 100 after the administration of the pharmaceutical composition.

13. The method of claim 5, wherein the human subject achieves a steady-state condition of the antibody within 40-50 days after administration.

14. The method of claim 5, wherein the administering of the anti-IFN-α/-ω antibody does not result in a treatment emergent adverse event (TEAE) related to a malignancy or anaphylactic or serum sickness-type reaction in the subject.

15. The method of claim 5, further comprising:
   a. assaying gene expression of one or more genes DHX58, EIF2AK2, HERC5, IFI44, IFI44L, IFI6, IRF7, PARP9, PLSCR1 and SAMD9L in a biological sample of the human subject; and
   b. identifying the human subject as responsive to treatment of the antibody prior to administering to the subject the pharmaceutical composition.

16. The method of claim 15, comprising:
   a. assaying gene expression of genes DHX58, EIF2AK2, HERC5, IFI44, IFI44L, IFI6, IRF7, PARP9, PLSCR1 and SAMD9L in a biological sample of the human subject;
   b. determining a combined expression value of the genes DHX58, EIF2AK2, HERC5, IFI44, IFI44L, IFI6, IRF7, PARP9, PLSCR1 and SAMD9L in the biological sample; and
   c. identifying the human subject as responsive to treatment of the antibody when the combined expression value is equal to or higher than a threshold value.

17. The method of claim 5, wherein the human subject has been treated with chloroquine, hydroxychloroquine, methotrexate or systemic corticosteroids, or any combination thereof.

18. The method of claim 5, further comprising administering chloroquine, hydroxychloroquine, methotrexate or systemic corticosteroids, or any combination thereof to the human subject.

19. The method of claim 6, wherein the pharmaceutical composition is intravenously administered to the human subject every two weeks.

* * * * *